US012807598B2

(12) United States Patent
Griffin et al.

(10) Patent No.: US 12,807,598 B2
(45) Date of Patent: Nov. 24, 2026

(54) KCNT1 INHIBITORS AND METHODS OF USE

(71) Applicant: Praxis Precision Medicines, Inc., Boston, MA (US)

(72) Inventors: Andrew Mark Griffin, L'lle Bizard (CA); Gabriel Martinez Botella, Wayland, MA (US); Brian Edward Marron, Ada, MI (US); Ricardo Lira, East Lyme, CT (US)

(73) Assignee: Praxis Precision Medicines, Inc., Boston, MA (US)

( * ) Notice: Subject to any disclaimer, the term of this patent is extended or adjusted under 35 U.S.C. 154(b) by 587 days.

(21) Appl. No.: 18/258,418

(22) PCT Filed: Dec. 22, 2021

(86) PCT No.: PCT/US2021/064870

§ 371 (c)(1),
(2) Date: Jun. 20, 2023

(87) PCT Pub. No.: WO2022/140547

PCT Pub. Date: Jun. 30, 2022

(65) Prior Publication Data

US 2024/0043415 A1 Feb. 8, 2024

Related U.S. Application Data

(60) Provisional application No. 63/129,083, filed on Dec. 22, 2020.

(51) Int. Cl.
*C07D 413/12* (2006.01)
*C07D 413/14* (2006.01)

(52) U.S. Cl.
CPC ......... *C07D 413/12* (2013.01); *C07D 413/14* (2013.01)

(58) Field of Classification Search
CPC ...... C07D 413/12; C07D 413/14; A61P 25/08
See application file for complete search history.

(56) References Cited

U.S. PATENT DOCUMENTS

| | | | |
|---|---|---|---|
| 8,207,147 | B2 | 6/2012 | Fyfe et al. |
| 10,538,516 | B2 | 1/2020 | Yanagisawa et al. |
| 2020/0129538 | A1 | 4/2020 | Petrou |

FOREIGN PATENT DOCUMENTS

| | | | | |
|---|---|---|---|---|
| CN | 101228155 | A | | 7/2008 |
| CN | 106831747 | A | | 6/2017 |
| JP | 2005060255 | A | * | 3/2005 |
| WO | 2020227097 | A1 | | 11/2020 |
| WO | 2020227101 | A1 | | 11/2020 |
| WO | 2021195066 | A2 | | 9/2021 |
| WO | 2022231873 | A1 | | 11/2022 |
| WO | 2023122152 | A1 | | 6/2023 |
| WO | 2023211850 | A1 | | 11/2023 |

OTHER PUBLICATIONS

PubChem SID 337471098 (which was deposited on Jun. 18, 2017). (Year: 2017).*

CAS Registry No. 1436359-23-7 (which entered the STN database on Jun. 9, 2013). (Year: 2013).*

Kim, H., (Authorized Officer), International Search Report and Written Opinion issued Jun. 9, 2022 in corresponding International Application No. PCT/US2021/064870, 10 pages.

National Center for Biotechnology Information (2023). PubChem Substance Record for SID 337471098, AKOS030455207, Source: AKos Consulting & Solutions. Modify Date: Jun. 3, 2019; Retrieved Jun. 14, 2023 from https://pubchem.ncbi.nlm.nih.gov/substance/337471098.

National Center for Biotechnology Information (2023). PubChem Substance Record for SID 375840372, NCGC00451897-01, Source: National Center for Advancing Translational Sciences (NCATS). Available Date: Sep. 7, 2018; Retrieved Jun. 14, 2023 from https://pubchem.ncbi.nlm.nih.gov/substance/375840372.

Rodriquez, Kari (PCT Authorized Officer), International Search Report and Written Opinion of the International Searching Authority for International Patent Application No. PCT/US2022/053609 dated May 4, 2023, 10 pages.

Rodriquez, Kari (PCT Authorized Officer), International Search Report and Written Opinion of the International Searching Authority for International Patent Application No. PCT/US2023/019648 dated Sep. 13, 2023, 11 pages.

Extended European Search Report mailed in EP 21912142.3 on Dec. 19, 2024 (5 pages).

* cited by examiner

*Primary Examiner* — Kamal A Saeed
*Assistant Examiner* — Meghan C Heasley
(74) *Attorney, Agent, or Firm* — MH2 Technology Law Group, LLP

(57) ABSTRACT

The present invention is directed to, in part, compounds and compositions useful for preventing and/or treating a neurological disease or disorder, a disease or condition relating to excessive neuronal excitability, and/or a gain-of-function mutation in a gene (e.g., KCNT1). Methods of treating a neurological disease or disorder, a disease or condition relating to excessive neuronal excitability, and/or a gain-of-function mutation in a gene such as KCNT1 are also provided herein.

6 Claims, No Drawings

KCNT1 INHIBITORS AND METHODS OF USE

CROSS-REFERENCE TO RELATED APPLICATIONS

This application is a U.S. National Stage Application of PCT/US2021/064870, filed Dec. 22, 2021, which claims priority to U.S. Provisional Patent Application No. 63/129,083 filed Dec. 22, 2020, which is incorporated herein by reference in its entirety.

BACKGROUND

KCNT1 encodes sodium-activated potassium channels known as Slack (Sequence like a calcium-activated $K^+$ channel). These channels are found in neurons throughout the brain and can mediate a sodium-activated potassium current $I_{KNa}$. This delayed outward current can regulate neuronal excitability and the rate of adaption in response to maintained stimulation. Abnormal Slack activity have been associated with development of early onset epilepsies and intellectual impairment. Accordingly, pharmaceutical compounds that selectively regulate sodium-activated potassium channels, e.g., abnormal KCNT1, abnormal $I_{KNa}$, are useful in treating a neurological disease or disorder or a disease or condition related to excessive neuronal excitability and/or KCNT1 gain-of-function mutations.

BRIEF SUMMARY

Described herein are compounds and compositions useful for preventing and/or treating a disease, disorder, or condition, e.g., a neurological disease or disorder, a disease, disorder, or condition associated with excessive neuronal excitability and/or a gain-of-function mutation in a gene, for example, KCNT1.

In one aspect, the present disclosure features a pharmaceutical composition comprising a compound of Formula I:

(I)

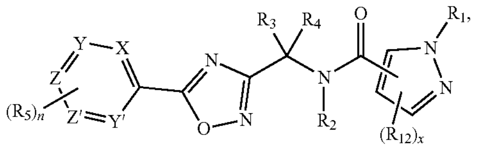

or a pharmaceutically acceptable salt thereof, wherein the variables are as defined herein, and a pharmaceutically acceptable excipient.

In certain embodiments, the compound is a compound of Formula I-a:

(I-a)

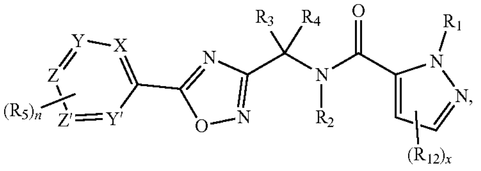

or a pharmaceutically acceptable salt thereof.

In some embodiments, the compound is a compound of Formula I-b:

(I-b)

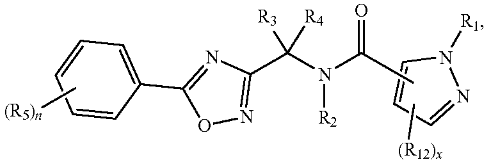

or a pharmaceutically acceptable salt thereof, wherein the variables are as defined herein.

In some embodiments, the compound is a compound of Formula I-c:

(I-c)

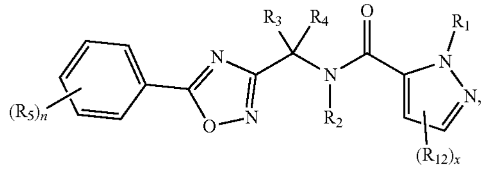

or a pharmaceutically acceptable salt thereof, wherein the variables are as defined herein.

In another aspect, provided herein is a compound of Formula II:

(II)

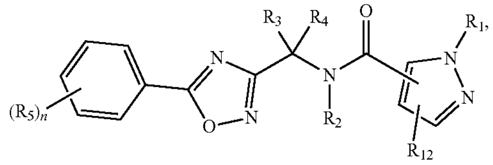

or a pharmaceutically acceptable salt thereof, wherein the variables are as defined herein.

In another aspect, the present invention provides a method of treating a neurological disease or disorder, wherein the method comprises administering to a subject in need thereof a compound of Formula I:

(I)

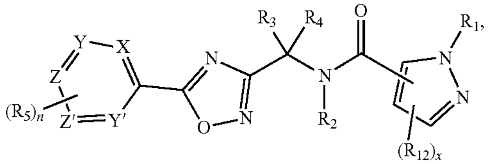

or a pharmaceutically acceptable salt thereof, wherein the variables are as defined herein.

In another aspect, provided herein is a method of treating a disease or condition associated with excessive neuronal excitability, wherein the method comprises administering to a subject in need thereof a compound of Formula I:

(I)

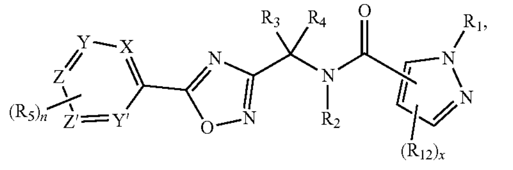

or a pharmaceutically acceptable salt thereof, wherein the variables are as defined herein.

Also provided herein is a method of treating a disease or condition associated with a gain-of-function mutation of a gene (e.g., KCNT1), wherein the method comprises administering to a subject in need thereof a compound of Formula I:

(I)

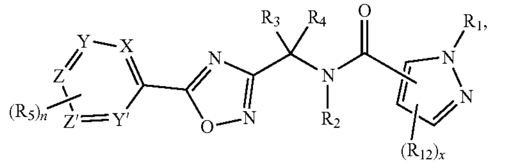

or a pharmaceutically acceptable salt thereof, wherein the variables are as defined herein.

Provided herein, in part, is a method of treating a neurological disease or disorder, wherein the method comprises administering to a subject in need thereof a compound or a pharmaceutical composition disclosed herein.

In another aspect, a method of treating a disease or condition associated with excessive neuronal excitability, wherein the method comprises administering to a subject in need thereof a compound or a pharmaceutical composition disclosed herein is provided.

A method of treating a disease or condition associated with a gain-of-function mutation of a gene (e.g., KCNT1), wherein the method comprises administering to a subject in need thereof a compound or a pharmaceutical composition disclosed herein is also provided.

In some embodiments, the neurological disease or disorder, the disease or condition associated with excessive neuronal excitability, or the disease or condition associated with a gain-of-function mutation of a gene (e.g., KCNT1) is epilepsy, an epilepsy syndrome, or an encephalopathy.

In other embodiments, the neurological disease or disorder, the disease or condition associated with excessive neuronal excitability, or the disease or condition associated with a gain-of-function mutation of a gene (e.g., KCNT1) is a genetic or pediatric epilepsy or a genetic or pediatric epilepsy syndrome.

In certain embodiments, the neurological disease or disorder, the disease or condition associated with excessive neuronal excitability, or the disease or condition associated with a gain-of-function mutation of a gene (e.g., KCNT1) is a cardiac dysfunction.

In some embodiments, the neurological disease or disorder, the disease or condition associated with excessive neuronal excitability, or the disease or condition associated with a gain-of-function mutation of a gene (e.g., KCNT1) is selected from the group consisting of epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, Lennox Gastaut syndrome, seizures (e.g., Generalized tonic clonic seizures, Asymmetric Tonic Seizures), leukodystrophy, leukoencephalopathy, intellectual disability, Multifocal Epilepsy, Drug resistant epilepsy, Temporal lobe epilepsy, or cerebellar ataxia).

In other embodiments, the neurological disease or disorder, the disease or condition associated with excessive neuronal excitability, or the disease or condition associated with a gain-of-function mutation of a gene (e.g., KCNT1) is selected from the group consisting of cardiac arrhythmia, sudden unexpected death in epilepsy, Brugada syndrome, and myocardial infarction.

In certain embodiments, the neurological disease or disorder, the disease or condition associated with excessive neuronal excitability, or the disease or condition associated with a gain-of-function mutation of a gene (e.g., KCNT1) is selected from pain and related conditions (e.g. neuropathic pain, acute/chronic pain, migraine).

In some embodiments, the neurological disease or disorder, the disease or condition associated with excessive neuronal excitability, or the disease or condition associated with a gain-of-function mutation of a gene (e.g., KCNT1) is a muscle disorder (e.g. myotonia, neuromyotonia, cramp muscle spasms, spasticity).

In other embodiments, the neurological disease or disorder, the disease or condition associated with excessive neuronal excitability, or the disease or condition associated with a gain-of-function mutation of a gene (e.g., KCNT1) is selected from itch and pruritis, ataxia and cerebellar ataxias.

In certain embodiments, the neurological disease or disorder, the disease or condition associated with excessive neuronal excitability, or the disease or condition associated with a gain-of-function mutation of a gene (e.g., KCNT1) is selected from psychiatric disorders (e.g. major depression, anxiety, bipolar disorder, schizophrenia).

In some embodiments, the neurological disease or disorder or the disease or condition associated with excessive neuronal excitability and/or a gain-of-function mutation in a gene (e.g., KCNT1) is selected from the group consisting of learning disorders, Fragile X, neuronal plasticity, and autism spectrum disorders.

In other embodiments, the neurological disease or disorder, the disease or condition associated with excessive neuronal excitability, or the disease or condition associated with a gain-of-function mutation of a gene (e.g., KCNT1) is selected from the group consisting of epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

Other objects and advantages will become apparent to those skilled in the art from a consideration of the ensuing Detailed Description, Examples, and Claims.

DETAILED DESCRIPTION

As generally described herein, the present invention provides compounds and compositions useful for preventing and/or treating a disease, disorder, or condition described herein, e.g., a disease, disorder, or condition associated with excessive neuronal excitability, and/or a disease, disorder, or condition associated with gain-of-function mutations in KCNT1. Exemplary diseases, disorders, or conditions include epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, and Lennox Gastaut syndrome, seizures, leukodystrophy, leukoencephalopathy, intellectual disability, Multifocal Epilepsy, Generalized tonic clonic seizures, Drug resistant epilepsy, Temporal lobe epilepsy, cerebellar ataxia, Asymmetric Tonic Seizures) and cardiac dysfunctions (e.g., cardiac arrhythmia, Brugada syndrome, sudden unexpected death in epilepsy, myocardial infarction), pain and related conditions (e.g. neuropathic pain, acute/chronic pain, migraine, etc), muscle disorders (e.g. myotonia, neuromyotonia, cramp muscle spasms, spasticity), itch and pruritis, ataxia and cerebellar ataxias, psychiatric disorders (e.g. major depression, anxiety, bipolar disorder, schizophrenia), learning disorders, Fragile X, neuronal plasticity, and autism spectrum disorders.

Definitions

Chemical Definitions

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^{1}$H, $^{2}$H (D or deuterium), and $^{3}$H (T or tritium); C may be in any isotopic form, including $^{12}$C, $^{13}$C, and $^{14}$C; O may be in any isotopic form, including $^{16}$O and $^{18}$O; F may be in any isotopic form, including $^{18}$F and $^{19}$F; and the like.

The following terms are intended to have the meanings presented therewith below and are useful in understanding the description and intended scope of the present invention. When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

As used herein, "alkylene," "alkenylene," and "alkynylene," refer to a divalent radical of an alkyl, alkenyl, and alkynyl group respectively. When a range or number of carbons is provided for a particular "alkylene," "alkenylene," or "alkynylene," group, it is understood that the range or number refers to the range or number of carbons in the linear carbon divalent chain. "Alkylene," "alkenylene," and "alkynylene," groups may be substituted or unsubstituted with one or more substituents as described herein.

As used herein, "aryl" refers to a radical of a monocyclic or polycyclic (e.g., bicyclic or tricyclic) 4n+2 aromatic ring system (e.g., having 6, 10, or 14 $\pi$ electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

As used herein, "heteroaryl" refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

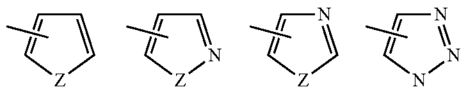

-continued

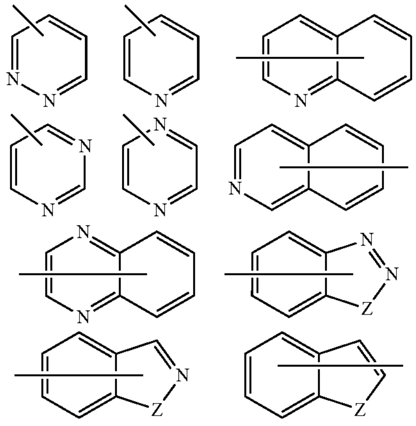

wherein each Z is selected from carbonyl, N, $NR^{65}$, O, and S; and $R^{65}$ is independently hydrogen, $C_1$-$C_8$ alkyl, $C_3$-$C_{10}$ carbocyclyl, 4-10 membered heterocyclyl, $C_6$-$C_{10}$ aryl, and 5-10 membered heteroaryl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. Cycloalkyl groups can be fused to other cycloalkyl, aryl, or heterocyclyl groups. In certain embodiments, the cycloalkyl group is not substituted, i.e., it is unsubstituted.

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

As used herein, "heterocylene" refers to a divalent radical of a heterocycle.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl; carbocyclyl, e.g., heterocyclyl; aryl, e.g., heteroaryl; and the like having from 1 to 5, and particularly from 1 to 3 heteroatoms.

As used herein, "cyano" refers to —CN.

As used herein, "halo" or "halogen" refers to fluoro (F), chloro (Cl), bromo (Br) and iodo (I). In certain embodiments, the halo group is either fluoro or chloro.

As used herein, "haloalkyl" refers to an alkyl group substituted with one or more halogen atoms.

As used herein, "nitro" refers to $—NO_2$.

As used herein, "oxo" refers to —C═O.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, $—OR^{aa}$, $—N(R^{cc})_2$, —CN, $—C(═O)R^{aa}$, $—C(═O)N(R^{cc})_2$, $—CO_2R^{aa}$, $—SO_2R^{aa}$, $—C(═NR^{bb})R^{aa}$, $—C(═NR^{cc})OR^{aa}$, $C(═NR^{cc})N(R^{cc})_2$, $—SO_2N(R^{cc})_2$, $—SO_2R^{cc}$, $—SO_2OR^{cc}$, $—SOR^{aa}$, $—C(═S)N(R^{cc})_2$, $—C(═O)SR^{cc}$, $—C(═S)SR^{cc}$, $—P(═O)_2R^{aa}$, $—P(═O)(R^{aa})_2$, $—P(═O)_2N(R^{cc})_2$, $—P(═O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and Claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19, and Gould, Salt selection for basic drugs, International Journal of Pharmaceutics, 33 (1986) 201-217. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition (also "therapeutic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

In an alternate embodiment, the present invention contemplates administration of the compounds of the present invention or a pharmaceutically acceptable salt or a pharmaceutically acceptable composition thereof, as a prophylactic before a subject begins to suffer from the specified disease, disorder or condition. As used herein, "prophylactic treatment" contemplates an action that occurs before a subject begins to suffer from the specified disease, disorder or condition. As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein, a "disease or condition associated with a gain-of-function mutation in KCNT1" refers to a disease or condition that is associated with, is partially or completely caused by, or has one or more symptoms that are partially or completely caused by, a mutation in KCNT1 that results in a gain-of-function phenotype, i.e. an increase in activity of the potassium channel encoded by KCNT1 resulting in an increase in whole cell current.

As used herein, a "gain-of-function mutation" is a mutation in KCNT1 that results in an increase in activity of the potassium channel encoded by KCNT1. Activity can be assessed by, for example, ion flux assay or electrophysiology (e.g. using the whole cell patch clamp technique). Typically, a gain-of-function mutation results in an increase of at least or about 20%, 30%, 40%, 50%, 60%, 70%, 80%, 90%, 100%, 125%, 150%, 175%, 200%, 225%, 250%, 275%, 300%, 325%, 350%, 375%, 400% or more compared to the activity of a potassium channel encoded by a wild-type KCNT1.

Compounds and Compositions

In one aspect, the present disclosure provides a pharmaceutical composition comprising a compound of Formula I:

(I)

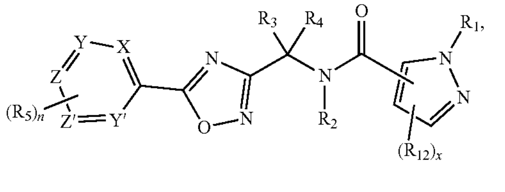

or a pharmaceutically acceptable salt thereof, wherein

- X, Y, Z, Y', and Z' are each independently selected from CH and N, wherein the hydrogen of CH may be substituted with $R_5$, wherein at least 3 selected from X, Y, Z, Y', and Z' are CH;
- $R_1$ is selected from the group consisting of $C_{1-6}$alkyl, $C_{3-10}$cycloalkyl, 3-10 membered heterocyclyl, 3-10 membered heteroaryl, and phenyl, wherein $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, C(O)N$(R_9)_2$, $N(R_9)_2$, $C_{3-7}$cycloalkyl, phenyl, 3-10 membered heteroaryl, and $C_{1-6}$alkoxy;
- $R_{12}$ is selected from the group consisting of $C_{1-6}$alkyl, $C_{3-10}$cycloalkyl, 3-10 membered heterocyclyl, 3-10 membered heteroaryl, and phenyl, wherein the $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, —OH, —CN, $C_{1-6}$alkyl, $C_{1-6}$haloalkyl, and $C_{1-6}$alkoxy; or two $R_{12}$ on adjacent carbons can be taken together with the two carbons where $R_{12}$ are attached to form a carbocyclic ring;
- x is 0, 1 or 2;
- $R_2$ is hydrogen or $C_{1-4}$alkyl;
- $R_3$ is selected from the group consisting of hydrogen, $C_{1-6}$alkyl, $C_{3-10}$ cycloalkyl, 3-10 membered heterocyclyl, 3-10 membered heteroaryl, and phenyl; and $R_4$ is selected from $C_{1-6}$alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$ cycloalkyl, 3-10 membered heterocyclyl, 3-10 membered heteroaryl, phenyl, $C_{3-7}$cycloalkylene, or 3-7 membered heterocyclene may be optionally substituted with one or more $R_7$;
- each $R_5$ is independently selected from the group consisting of halogen, $C_{1-6}$alkyl, $C_{1-6}$haloalkyl, $C_{1-6}$alkylene-$N(R_9)_2$, $C_{1-6}$alkylene-O—$C_{3-10}$cycloalkyl, $C_{1-6}$alkoxy, $C_{1-6}$alkoxy substituted with $C_{3-10}$cycloalkyl optionally substituted with one or more halogens, $C_{1-6}$haloalkoxy, 3-10 membered heterocyclyl optionally substituted with one or more halogens or $C_{1-6}$alkoxy, 3-10 membered heteroaryl, $C_{1-6}$alkylene-OH, $C_{1-6}$alkylene-$C_{1-6}$ alkoxy, OH, $N(R_9)_2$, —C(O)$OR_8$, C(O)$N(R_9)_2$, $C_{1-6}$alkylene-CN, —CN, —$S(O)_2$—$C_{1-6}$alkyl, $C_{1-6}$alkylene-$S(O)_2$—$C_{1-6}$alkyl, —$S(O)_2$—$N(R_9)_2$, —OC(O)$C_{1-6}$alkyl, —O—$C_{3-10}$cycloalkyl optionally substituted with one or more halogen or $C_{1-6}$alkyl, and $C_{3-10}$cycloalkyl optionally substituted with one or more substituents selected from halogen, $C_{1-6}$alkyl, and $C_{1-6}$alkoxy;
- n is selected from the group consisting of 0, 1, 2, and 3;
- $R_7$ is each independently selected from the group consisting of phenyl, $C_{1-6}$alkoxy, —OH, —$N(R_9)_2$, —$NR_9$—$SO_2$—$C_{1-6}$alkyl, —O—($C_{1-6}$alkylene)-phenyl, $C_{3-10}$cycloalkyl, —C(O)$OR_8$, —C(O)$N(R_9)_2$, —$NR_{10}$C(O)—$R_{11}$, —CN, —$S(O)_2$—$C_{1-6}$alkyl, —$S(O)_2$—$N(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —$N(R_9)_2$;
- $R_8$ is hydrogen or $C_{1-6}$alkyl;
- each $R_9$ is independently selected from the group consisting of hydrogen, $C_{1-6}$alkyl, and —($C_{1-6}$alkylene)—OH, or the two $R_9$ can be taken together with the nitrogen atom attached to the two $R_9$ to form a heterocycle optionally substituted with one or more substituents each independently selected from halogen and —OH;
- each $R_{10}$ is independently hydrogen or $C_{1-6}$alkyl;
- $R_{11}$ is selected from the group consisting of $C_{1-6}$alkyl, $C_{1-6}$alkoxy, and —O—($C_{1-6}$alkylene)-phenyl; and
- when $R_3$ and $R_4$ are both hydrogen, at least one selected from X, Y, Z, Y', and Z' is N; and a pharmaceutically acceptable excipient.

In some embodiments, one of X, Y, Z, Y', and Z' is N and the other four are CH.

In certain embodiments, the compound is a compound of Formula I-a:

(I-a)

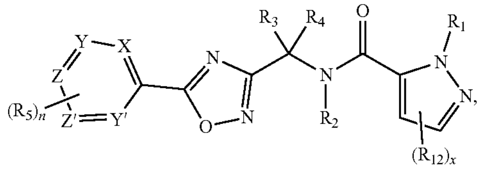

or a pharmaceutically acceptable salt thereof, wherein the variables are as defined herein.

In other embodiments, the compound is a compound of Formula I-b:

(I-b)

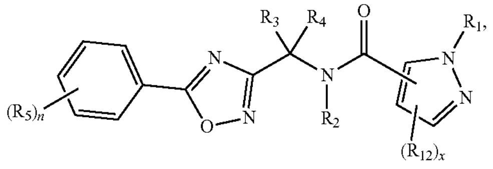

or a pharmaceutically acceptable salt thereof, wherein the variables are as defined herein.

In certain embodiments, the compound is a compound of Formula I-c:

(I-c)

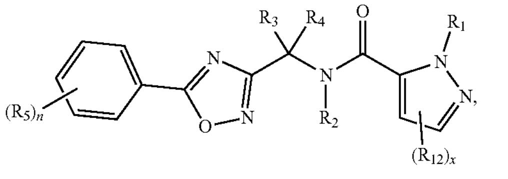

or a pharmaceutically acceptable salt thereof, wherein the variables are as defined herein.

In some embodiments, $R_2$ is hydrogen. In other embodiments, $R_2$ is methyl.

In certain embodiments, $R_3$ is hydrogen. In some embodiments, $R_3$ is $C_{1-6}$alkyl. In other embodiments, $R_3$ is selected from the group consisting of methyl, ethyl, and isopropyl. In some embodiments, $R_3$ is methyl. In other embodiments, $R_3$ is ethyl. In certain embodiments, $R_3$ is $C_{1-6}$alkyl substituted with $C_{1-6}$alkoxy, —OH, or —C(O)$OR_8$.

In some embodiments, $R_4$ is hydrogen. In other embodiments, $R_3$ and $R_4$ are taken together with the carbon attached to $R_3$ and $R_4$ to form a $C_{3-7}$cycloalkylene or 3-7 membered heterocyclene. In certain embodiments, the $C_{3-7}$cycloalkylene is selected from the group consisting of cyclopropyl, cyclobutyl, cyclopentyl, and cyclohexyl. In certain embodiments, the 3-7 membered heterocyclene is selected from the group consisting of oxetanyl, tetrahydrofuranyl, and tetrahydropyranyl.

In some embodiments, each $R_5$ is independently selected from the group consisting of halogen, $C_{1-6}$alkyl, $C_{1-6}$haloalkyl, $C_{1-6}$alkoxy, $C_{1-6}$haloalkoxy, $C_{3-10}$cycloalkyl, O—$C_{3-10}$cycloalkyl, —OH, —CN, $N(R_9)_2$, and —C(O)$OR_8$. In other embodiments, $R_5$ is methyl. In certain embodiments, each $R_5$ is halogen. In some embodiments, $R_5$ is —F. In other embodiments, $R_5$ is —Cl. In certain embodiments, $R_5$ is methoxy. In some embodiments, $R_5$ is —$CF_3$. In other embodiments, $R_5$ is —$CHF_2$. In certain embodiments, each $R_5$ is —C(O)$OR_8$. In some embodiments, each $R_5$ is cyclopropyl, cyclobutyl, or cyclopentyl.

In other embodiments, n is 1. In some embodiments, n is 2. In certain embodiments, n is 1 and $R_5$ is at the meta-position. In other embodiments, n is 2 and the two $R_5$ are at the ortho- and para- positions. In some embodiments, n is 2 and the two $R_5$ are at the meta- and para- positions. In certain embodiments, n is 2 and the two $R_5$ are at the meta-positions.

In some embodiments, $R_1$ is selected from the group consisting of $C_{1-6}$alkyl optionally substituted with $C_{1-6}$alkoxy, $N(R_9)_2$, $C(O)N(R_9)_2$, $C_{3-7}$cycloalkyl, pyridyl, tetrahydropyranyl, or phenyl, $C_{1-6}$haloalkyl, $C_{3-7}$cycloalkyl, phenyl optionally substituted with halogen, and pyridyl optionally substituted with halogen. In other embodiments, $R_1$ is $C_{1-6}$alkyl. In certain embodiments, $R_1$ is methyl. In some embodiments, $R_1$ is ethyl. In other embodiments, $R_1$ is $C_{1-6}$haloalkyl. In certain embodiments, $R_1$ is —$CH_2$—$CHF_2$. In some embodiments, $R_1$ is —$CHF_2$. In other embodiments, $R_1$ is $C_{3-7}$cycloalkyl. In certain embodiments, $R_1$ is cyclopropyl. In some embodiments, $R_1$ is cyclobutyl. In other embodiments, $R_1$ is $C_{1-6}$alkyl substituted with $C_{1-6}$alkoxy. In certain embodiments, $R_1$ is $C_{1-6}$alkyl substituted with methoxy. In some embodiments, $R_1$ is $C_{1-6}$alkyl substituted with $C_{3-7}$cycloalkyl. In other embodiments, $R_1$ is $C_{1-6}$alkyl substituted with cyclopropyl. In certain embodiments, $R_1$ is phenyl substituted with halogen.

In some embodiments, $R_{12}$ is selected from the group consisting of $C_{1-6}$alkyl, $C_{1-6}$haloalkyl, $C_{3-7}$cycloalkyl, and phenyl optionally substituted with halogen. In other embodiments, $R_{12}$ is $C_{3-7}$cycloalkyl. In certain embodiments, $R_{12}$ is cyclopropyl. In some embodiments, $R_{12}$ is $C_{1-6}$alkyl. In other embodiments, $R_{12}$ is ethyl. In certain embodiments, $R_{12}$ is methyl. In some embodiments, $R_{12}$ is t-butyl. In other embodiments, $R_{12}$ is isopropyl. In certain embodiments, $R_{12}$ is $C_{1-6}$haloalkyl. In other embodiments, $R_{12}$ is —$CF_3$. In some embodiments, $R_{12}$ is —$CHF_2$. In other embodiments, $R_{12}$ is phenyl optionally substituted with —F.

In certain embodiments, x is 1. In other embodiments, x is 2.

In another aspect, provided herein is a compound of Formula II.

(II)

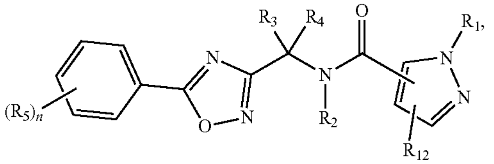

or a pharmaceutically acceptable salt thereof, wherein $R_1$ is $C_{1-6}$alkyl or $C_{3-7}$cycloalkyl, wherein the $C_{1-6}$alkyl or $C_{3-7}$cycloalkyl is optionally substituted with one or more substituents independently selected from halogen and $C_{1-6}$alkoxy;

$R_{12}$ is $C_{1-6}$alkyl optionally substituted with one or more halogen or $C_{1-6}$alkoxy;

$R_2$ is hydrogen or $C_{1-4}$alkyl;

$R_3$ is selected from the group consisting of $C_{1-6}$alkyl, $C_{3-10}$ cycloalkyl, 3-10 membered heterocyclyl, 3-10 membered heteroaryl, and phenyl; and $R_4$ is selected from $C_{1-6}$alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$ cycloalkyl, 3-10 membered heterocyclyl, 3-10 membered heteroaryl, phenyl, $C_{3-7}$cycloalkylene or 3-7 membered heterocyclene may be optionally substituted with $R_7$;

$R_5$ is selected from the group consisting of halogen, $C_{1-6}$alkyl, $C_{1-6}$alkoxy, $C_{1-6}$haloalkyl, $C_{1-6}$haloalkoxy, 3-10 membered heterocyclyl, 3-10 membered heteroaryl, —$C_{1-6}$alkylene-OH, OH, —C(O)$OR_8$, —C(O)$N(R_9)_2$, —$C_{1-6}$alkylene-CN, —CN, —$S(O)_2$—$C_{1-6}$alkyl, $C_{1-6}$alkylene-$S(O)_2$—$C_{1-6}$alkyl, —$S(O)_2$—$N(R_9)_2$, —OC(O)$C_{1-6}$alkyl, and —O—$C_{3-10}$cycloalkyl optionally substituted with one or more halogen;

$R_7$ is each independently selected from the group consisting of phenyl, $C_{1-6}$alkoxy, —OH, —O—($C_{1-6}$alkylene)-phenyl, $C_{3-10}$cycloalkyl, —C(O)$OR_8$, —C(O)$N(R_9)_2$, —$NR_{10}$C(O)—$R_{11}$, —CN, —$S(O)_2$—$C_{1-6}$ alkyl, —$S(O)_2$—$N(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —$N(R_9)_2$;

$R_8$ is hydrogen or $C_{1-6}$alkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents selected from halogen and —OH;

each $R_{10}$ is independently hydrogen or $C_{1-6}$alkyl;

$R_1$ is selected from the group consisting of $C_{1-6}$alkyl, $C_{1-6}$alkoxy, and —O—($C_{1-6}$alkylene)-phenyl; and n is selected from the group consisting of 0, 1, 2, and 3.

In some embodiments, $R_2$ is hydrogen.

In other embodiments, $R_3$ is $C_{1-6}$alkyl. In certain embodiments, $R_3$ is methyl. In some embodiments, $R_3$ is ethyl. In other embodiments, $R_3$ is $C_{1-6}$alkyl substituted with $C_{1-6}$alkoxy. In certain embodiments, $R_4$ is hydrogen. In some embodiments, $R_3$ and $R_4$ are taken together with the carbon attached to $R_3$ and $R_4$ to form a $C_{3-7}$cycloalkylene or 3-7 membered heterocyclene.

In some embodiments, each $R_5$ is methyl. In other embodiments, each $R_5$ is halogen. In certain embodiments, each $R_5$ is —F. In some embodiments, each $R_5$ is —Cl. In other embodiments, each $R_5$ is methoxy. In certain embodiments, each $R_5$ is —$CF_3$. In some embodiments, each $R_5$ is —$CHF_2$. In other embodiments, $R_5$ is —C(O)O$R_8$.

In certain embodiments, n is 1. In some embodiments, n is 2.

In other embodiments, n is 1 and $R_5$ is at the meta-position.

In some embodiments, n is 2 and the two $R_5$ are at the ortho- and para- positions.

In other embodiments, n is 2 and the two $R_5$ are at the meta- and para- positions.

In certain embodiments, n is 2 and the two $R_5$ are at the meta-positions.

In some embodiments, $R_1$ is $C_{1-6}$alkyl. In certain embodiments, $R_1$ is methyl. In other embodiments, $R_1$ is ethyl. In some embodiments, $R_1$ is $C_{1-6}$haloalkyl. In other embodiments, $R_1$ is —$CH_2$—$CHF_2$. In certain embodiments, $R_1$ is —$CHF_2$. In some embodiments, $R_1$ is $C_{3-7}$cycloalkyl. In other embodiments, $R_1$ is cyclopropyl.

In certain embodiments, $R_{12}$ is $C_{1-6}$alkyl. In some embodiments, $R_{12}$ is ethyl. In other embodiments, $R_{12}$ is methyl. In certain embodiments, $R_{12}$ is t-butyl. In some embodiments, $R_{12}$ is $C_{1-6}$haloalkyl. In other embodiments, $R_{12}$ is —$CF_3$. In certain embodiments, $R_{12}$ is —$CHF_2$.

In other aspects, provided is a compound of Formula III:

(III)

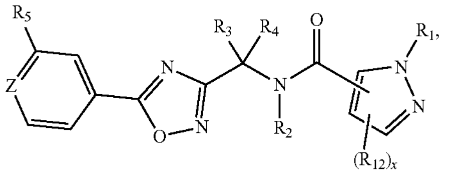

or a pharmaceutically acceptable salt thereof, wherein $R_1$, $R_{12}$, x, $R_2$, $R_3$, $R_4$, $R_5$ and Z are as defined for Formula I above as applicable.

In some embodiments, Z is CH or N. In one variation, Z is CH. In another variation, Z is N.

In some embodiments, $R_1$ is $C_{1-6}$alkyl. In certain embodiments, $R_1$ is methyl.

In certain embodiments, $R_{12}$ is $C_{1-6}$haloalkyl. In other embodiments, $R_{12}$ is —$CF_3$. In certain embodiments, $R_{12}$ is —$CHF_2$. In some variations, x is 1.

In other embodiments, $R_3$ is $C_{1-6}$alkyl. In certain embodiments, $R_3$ is methyl. In certain embodiments, $R_4$ is hydrogen.

In some embodiments, $R_5$ is $C_{1-6}$alkyl. In certain embodiments, $R_5$ is methyl. In other embodiments, $R_5$ is $C_{3-6}$ cycloalkyl. In certain embodiments, $R_5$ is cyclopropyl.

In one aspect, provided is a compound of Formula (III-a):

(III-a)

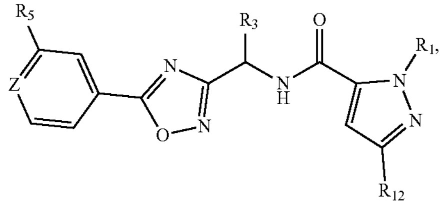

or a pharmaceutically acceptable salt thereof, wherein $R_1$, $R_{12}$, $R_3$, $R_5$ and Z are as defined for Formula I or III above as applicable.

In some aspects, provided is a compound in Table A below, or a pharmaceutically acceptable salt thereof.

TABLE A

| Patent Compound No. | Structure |
|---|---|
| 1 | 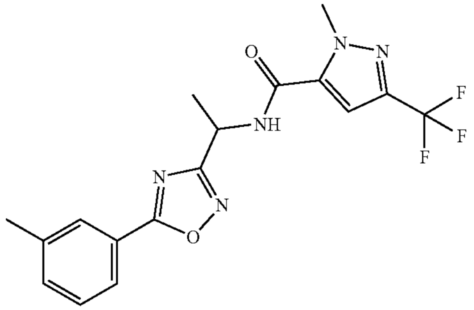 [SMILES: Cc1cccc(-c2nc(C(C)NC(=O)c3cc(C(F)(F)F)nn3C)no2)c1] |
| 2 | 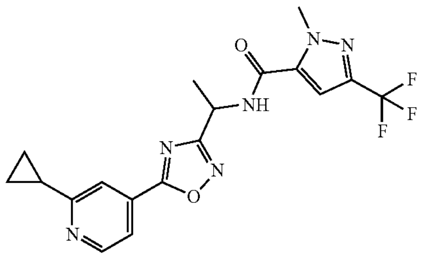 [SMILES: CC(NC(=O)c1cc(C(F)(F)F)nn1C)c1noc(-c2ccnc(C3CC3)c2)n1] |
| 2a | 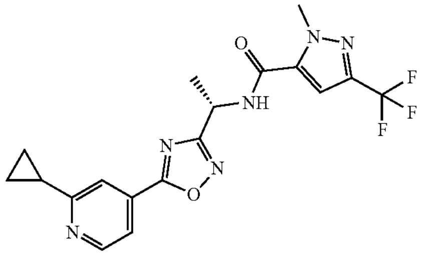 [SMILES: C[C@H](NC(=O)c1cc(C(F)(F)F)nn1C)c1noc(-c2ccnc(C3CC3)c2)n1] |

In some variations of Table A above, provided is an enantiomer of Compound 1 and 2, or a pharmaceutically acceptable salt thereof. In certain variations, the enantiomer is optically active. In one variation, the enantiomer is the (S)-enantiomer. In another variation, the enantiomer is the (R)-enantiomer.

In certain aspects, provided is a composition comprising an optically active form of any of the compounds described herein (as applicable). In some variations, the composition comprises a single enantiomer. In certain variations, the composition comprises the (R)-enantiomer. In other variations, the composition comprises the (S)-enantiomer.

In other aspects, provided is a pharmaceutical composition comprising any of the compounds described herein, or a pharmaceutically acceptable salt thereof, and at least one pharmaceutically acceptable excipient.

General Synthetic Schemes

Exemplary methods for preparing compounds described herein are illustrated in the following synthetic schemes. These schemes are given for the purpose of illustrating the invention, and should not be regarded in any manner as limiting the scope or the spirit of the invention.

The synthetic route illustrated in Scheme 1 depicts an exemplary procedure for preparing carboxylic acid intermediate D. In the first step, compound A is reacted with hydrazine B to form ethyl pyrazole-5-carboxylate C. Then, hydrolysis of C provides carboxylic acid D.

SCHEME 1

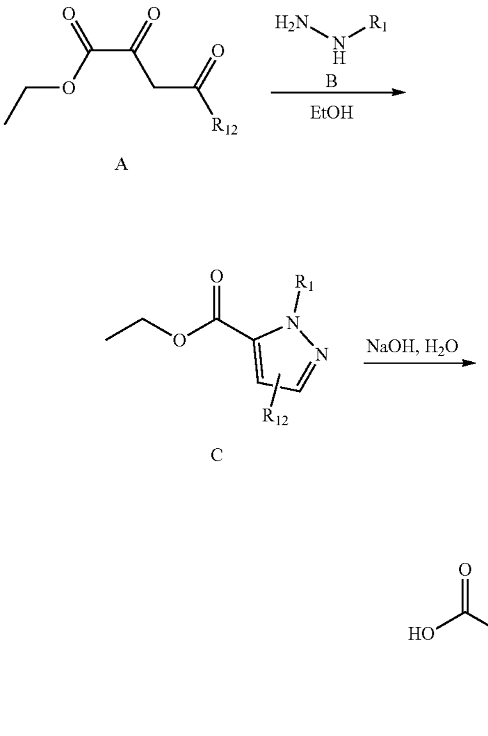

A

C

D

The synthetic route illustrated in Scheme 2 depicts an exemplary procedure for preparing amine-substituted oxadiazole intermediate I. Starting material E is commercially available or can be prepared from a commercially available material. Intermediate F is synthesized in a few steps from E using protocols similar to the procedures described in Example 1. Intermediate F is reacted with acyl chloride G in the presence of pyridine and DMAP to afford oxadiazole H. Deprotection of H under acidic conditions provides amine-substituted oxadiazole intermediate I.

SCHEME 2

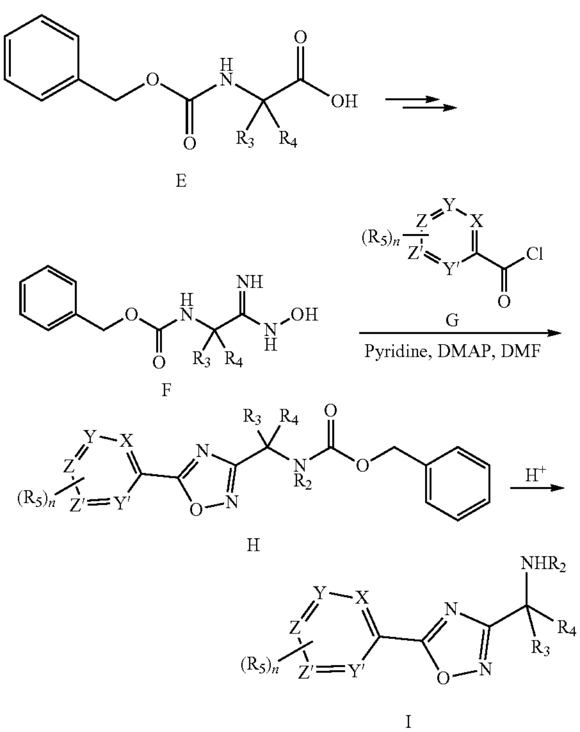

E

F

H

I

The synthetic route illustrated in Scheme 3 depicts an exemplary procedure for preparing J (a compound of Formula I-a). Coupling of amine-substituted oxadiazole amine I with carboxylic acid D using standard peptide coupling procedures (e.g., HATU and DIPEA in DMF) provides compound J (a compound of Formula I-a). Similar procedures may be used to prepare a compound of Formula I.

SCHEME 3

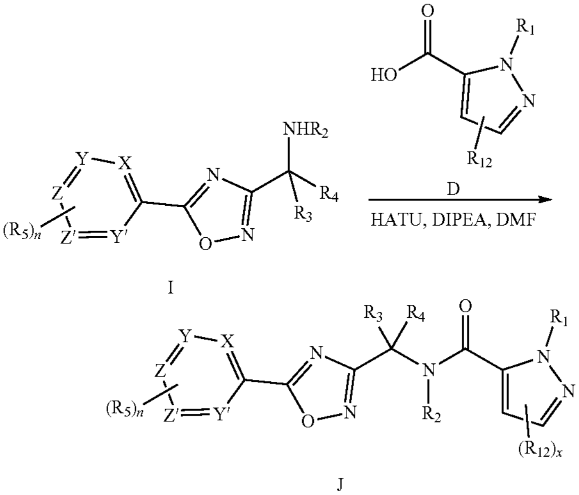

I

J

Methods of Treatment

The compounds and compositions described above and herein can be used to treat a neurological disease or disorder or a disease or condition associated with excessive neuronal excitability and/or a gain-of-function mutation in a gene (e.g., KCNT1). Exemplary diseases, disorders, or conditions include epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, developmental and epileptic encephalopathy (DEE), early infantile epileptic encephalopathy (EIEE), generalized epilepsy, focal epilepsy, multifocal epilepsy, temporal lobe epilepsy, Ohtahara syndrome, early myoclonic encephalopathy and Lennox Gastaut syndrome, drug resistant epilepsy, seizures (e.g., frontal lobe seizures, generalized tonic clonic seizures, asymmetric tonic seizures, focal seizures), leukodystrophy, hypomyelinating leukodystrophy, leukoencephalopathy, and sudden unexpected death in epilepsy, cardiac dysfunctions (e.g., cardiac arrhythmia, Brugada syndrome, myocardial infarction), pulmonary vasculopathy/hemorrhage, pain and related conditions (e.g. neuropathic pain, acute/chronic pain, migraine, etc), muscle disorders (e.g. myotonia, neuromyotonia, cramp muscle spasms, spasticity), itch and pruritis, movement disorders (e.g., ataxia and cerebellar ataxias), psychiatric disorders (e.g. major depression, anxiety, bipolar disorder, schizophrenia, attention-deficit hyperactivity disorder), neurodevelopmental disorder, learning disorders, intellectual disability, Fragile X, neuronal plasticity, and autism spectrum disorders.

In some embodiments, the neurological disease or disorder or the disease or condition associated with excessive neuronal excitability and/or a gain-of-function mutation in a gene (e.g., KCNT1) is selected from EIMFS, ADNFLE and West syndrome. In some embodiments, the neurological disease or disorder or the disease or condition associated with excessive neuronal excitability and/or a gain-of-function mutation in a gene (e.g., KCNT1) is selected from infantile spasms, epileptic encephalopathy, focal epilepsy, Ohtahara syndrome, developmental and epileptic encephalopathy and Lennox Gastaut syndrome. In some embodiments, the neurological disease or disorder or the disease or condition associated with excessive neuronal excitability and/or a gain-of-function mutation in a gene (e.g., KCNT1) is seizure. In some embodiments, the neurological disease or disorder or the disease or condition associated with excessive neuronal excitability and/or a gain-of-function mutation in a gene (e.g., KCNT1) is selected from cardiac arrhythmia, Brugada syndrome, and myocardial infarction.

In some embodiments, the neurological disease or disorder or the disease or condition associated with excessive neuronal excitability and/or a gain-of-function mutation in a gene (e.g., KCNT1) is selected from the group consisting of the learning disorders, Fragile X, intellectual function, neuronal plasticity, psychiatric disorders, and autism spectrum disorders.

Accordingly, the compounds and compositions thereof can be administered to a subject with a neurological disease or disorder or a disease or condition associated with excessive neuronal excitability and/or a gain-of-function mutation in a gene such as KCNT1 (e.g., EIMFS, ADNFLE, West syndrome, infantile spasms, epileptic encephalopathy, focal epilepsy, Ohtahara syndrome, developmental and epileptic encephalopathy, and Lennox Gastaut syndrome, seizures, cardiac arrhythmia, Brugada syndrome, and myocardial infarction).

EIMFS is a rare and debilitating genetic condition characterized by an early onset (before 6 months of age) of almost continuous heterogeneous focal seizures, where seizures appear to migrate from one brain region and hemisphere to another. Patients with EIMFS are generally intellectually impaired, non-verbal and non-ambulatory. While several genes have been implicated to date, the gene that is most commonly associated with EIMFS is KCNT1. Several de novo mutations in KCNT1 have been identified in patients with EIMFS, including V271F, G288S, R428Q, R474Q, R474H, R474C, I760M, A934T, P924L, G243S, H257D, A259D, R262Q, Q270E, L2741, F346L, C377S, R398Q, P409S, A477T, F502V, M516V, Q550del, K629E, K629N, I760F, E893K, M896K, R933G, R950Q, K1154Q (Barcia et al. (2012) Nat Genet. 44: 1255-1260; Ishii et al. (2013) Gene 531:467-471; McTague et al. (2013) Brain. 136: 1578-1591; Epi4K Consortium & Epilepsy Phenome/Genome Project. (2013) Nature 501:217-221; Lim et al. (2016) Neurogenetics; Ohba et al. (2015) Epilepsia 56:e121-e128; Zhou et al. (2018) Genes Brain Behav. e12456; Moller et al. (2015) Epilepsia. e114-20; Numis et al. (2018) Epilepsia. 1889-1898; Madaan et al. Brain Dev. 40(3):229-232; McTague et al. (2018) Neurology. 90(1):e55-e66; Kawasaki et al. (2017) J Pediatr. 191:270-274; Kim et al. (2014) Cell Rep. 9(5):1661-1672; Ohba et al. (2015) Epilepsia. 56(9):e121-8; Rizzo et al. (2016) Mol Cell Neurosci. 72:54-63; Zhang et al. (2017) Clin Genet. 91(5):717-724; Mikati et al. (2015) Ann Neurol. 78(6):995-9; Baumer et al. (2017) Neurology. 89(21):2212; Dilena et al. (2018) Neurotherapeutics. 15(4):1112-1126). These mutations are gain-of-function, missense mutations that are dominant (i.e. present on only one allele) and result in change in function of the encoded potassium channel that causes a marked increase in whole cell current when tested in *Xenopus* oocyte or mammalian expression systems (see e.g. Milligan et al. (2015) Ann Neurol. 75(4): 581-590; Barcia et al. (2012) Nat Genet. 44(11): 1255-1259; and Mikati et al. (2015) Ann Neurol. 78(6): 995-999).

ADNFLE has a later onset than EIMFS, generally in mid-childhood, and is generally a less severe condition. It is characterized by nocturnal frontal lobe seizures and can result in psychiatric, behavioural and cognitive disabilities in patients with the condition. While ADNFLE is associated with genes encoding several neuronal nicotinic acetylcholine receptor subunits, mutations in the KCNT1 gene have been implicated in more severe cases of the disease (Heron et al. (2012) Nat Genet. 44: 1188-1190). Functional studies of the mutated KCNT1 genes associated with ADNFLE indicated that the underlying mutations (M896I, R398Q, Y796H and R928C) were dominant, gain-of-function mutations (Milligan et al. (2015) Ann Neurol. 75(4): 581-590; Mikati et al. (2015) Ann Neurol. 78(6): 995-999).

West syndrome is a severe form of epilepsy composed of a triad of infantile spasms, an interictal electroencephalogram (EEG) pattern termed hypsarrhythmia, and mental retardation, although a diagnosis can be made one of these elements is missing. Mutations in KCNT1, including G652V and R474H, have been associated with West syndrome (Fukuoka et al. (2017) Brain Dev 39:80-83 and Ohba et al. (2015) Epilepsia 56:e121-e128). Treatment targeting the KCNT1 channel suggests that these mutations are gain-of-function mutations (Fukuoka et al. (2017) Brain Dev 39:80-83).

In one aspect, the present invention features a method of treating treat a disease or condition associated with excessive neuronal excitability and/or a gain-of-function mutation in a gene such as KCNT1 (for example, epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy (DEE), and Lennox Gastaut syndrome, seizures, leukodystrophy, leukoencephalopathy, intellectual disability, Multifocal Epilepsy, Generalized tonic clonic seizures, Drug resistant epilepsy, Temporal lobe epilepsy, cerebellar ataxia, Asymmetric Tonic Seizures) and cardiac dysfunctions (e.g., cardiac arrhythmia, Brugada syndrome, sudden unexpected death in epilepsy, myocardial infarction), pain and related conditions (e.g. neuropathic pain, acute/chronic pain, migraine, etc), muscle disorders (e.g. myotonia, neuromyotonia, cramp muscle spasms, spasticity), itch and pruritis, ataxia and cerebellar ataxias, psychiatric disorders (e.g. major depression, anxiety, bipolar disorder, schizophrenia), learning disorders, Fragile X, neuronal plasticity, and autism spectrum disorders) comprising administering to a subject in need thereof a compound disclosed herein (e.g., a compound of Formula (I), (e.g., (I-a), (I-b)) or (II) or a pharmaceutically acceptable salt thereof) or a pharmaceutical composition disclosed herein (e.g., a pharmaceutical composition comprising a compound disclosed herein (e.g., a compound of Formula (I), (e.g., (I-a), (I-b)) or (II) or a pharmaceutically acceptable salt thereof), and a pharmaceutically acceptable excipient).

In some examples, the subject presenting with a disease or condition that may be associated with a gain-of-function mutation in KCNT1 is genotyped to confirm the presence of a known gain-of-function mutation in KCNT1 prior to administration of the compounds and compositions thereof. For example, whole exome sequencing can be performed on the subject. Gain-of-function mutations associated with EIMFS may include, but are not limited to, V271F, G288S, R428Q, R474Q, R474H, R474C, I760M, A934T, P924L, G243S, H257D, A259D, R262Q, Q270E, L2741, F346L, C377S, R398Q, P409S, A477T, F502V, M516V, Q550del, K629E, K629N, I760F, E893K, M896K, R933G, R950Q, and K1154Q. Gain-of-function mutations associated with ADNFLE may include, but are not limited to, M896I, R398Q, Y796H, R928C, and G288S. Gain-of-function mutations associated with West syndrome may include, but are not limited to, G652V and R474H. Gain-of-function mutations associated with temporal lobe epilepsy may include, but are not limited to, R133H and R565H. Gain-of-function mutations associated with Lennox-Gastaut may include, but are not limited to, R209C. Gain-of-function mutations associated with seizures may include, but are not limited to, A259D, G288S, R474C, R474H. Gain-of-function mutations associated with leukodystrophy may include, but are not limited to, G288S and Q906H. Gain-of-function mutations associated with Multifocal Epilepsy may include, but are not limited to, V340M. Gain-of-function mutations associated with EOE may include, but are not limited to, F346L and A934T. Gain-of-function mutations associated with Early-onset epileptic encephalopathies (EOEE) may include, but are not limited to, R428Q. Gain-of-function mutations associated with developmental and epileptic encephalopathies may include, but are not limited to, F346L, R474H, and A934T. Gain-of-function mutations associated with epileptic encephalopathies may include, but are not limited to, L437F, Y796H, P924L, R961H. Gain-of-function mutations associated with Early Infantile Epileptic Encephalopathy (EIEE) may include, but are not limited to, M896K. Gain-of-function mutations associated with drug resistant epilepsy and generalized tonic-clonic seizure may include, but are not limited to, F346L. Gain-of-function mutations associated with migrating partial seizures of infancy may include, but are not limited to, R428Q. Gain-of-function mutations associated with Leukoencephalopathy may include, but are not limited to, F9321. Gain-of-function mutations associated with NFLE may include, but are not limited to, A934T and R950Q. Gain-of-function mutations associated with Ohtahara syndrome may include, but are not limited to, A966T. Gain-of-function mutations associated with infantile spasms may include, but are not limited to, P924L. Gain-of-function mutations associated with Brugada Syndrome may include, but are not limited to, R1106Q. Gain-of-function mutations associated with Brugada Syndrome may include, but are not limited to, R474H.

In other examples, the subject is first genotyped to identify the presence of a mutation in KCNT1 and this mutation is then confirmed to be a gain-of-function mutation using standard in vitro assays, such as those described in Milligan et al. (2015) Ann Neurol. 75(4): 581-590. Typically, the presence of a gain-of-function mutation is confirmed when the expression of the mutated KCNT1 allele results an increase in whole cell current compared to the whole cell current resulting from expression of wild-type KCNT1 as assessed using whole-cell electrophysiology (such as described in Milligan et al. (2015) Ann Neurol. 75(4): 581-590; Barcia et al. (2012) Nat Genet. 44(11): 1255-1259; Mikati et al. (2015) Ann Neurol. 78(6): 995-999; or Rizzo et al. Mol Cell Neurosci. (2016) 72:54-63). This increase of whole cell current can be, for example, an increase of at least or about 50%, 100%, 150%, 200%, 250%, 300%, 350%, 400% or more. The subject can then be confirmed to have a disease or condition associated with a gain-of-function mutation in KCNT1.

In particular examples, the subject is confirmed as having a KCNT1 allele containing a gain-of-function mutation (e.g. V271F, G288S, R398Q, R428Q, R474Q, R474H, R474C, G652V, I760M, Y796H, M896I, P924L, R928C or A934T).

The compounds disclosed herein (e.g., a compound of Formula (I), (e.g., (I-a), (I-b), (I-c)) or (II) or a pharmaceutically acceptable salt thereof) or the pharmaceutical composition disclosed herein (e.g., a pharmaceutical composition comprising a compound disclosed herein (e.g., a compound of Formula (I), (e.g., (I-a), (I-b), (I-c)) or (II) or a pharmaceutically acceptable salt thereof), and a pharmaceutically acceptable excipient) can also be used therapeutically for conditions associated with excessive neuronal excitability where the excessive neuronal excitability is not necessarily the result of a gain-of-function mutation in KCNT1. Even in instances where the disease is not the result of increased KCNT1 expression and/or activity, inhibition of KCNT1 expression and/or activity can nonetheless result in a reduction in neuronal excitability, thereby providing a therapeutic effect. Thus, the compounds disclosed herein (e.g., a compound of Formula (I), (e.g., (I-a), (I-b)) or (II) or a pharmaceutically acceptable salt thereof) or the pharmaceutical composition disclosed herein (e.g., a pharmaceutical composition comprising a compound disclosed herein (e.g., a compound of Formula (I), (e.g., (I-a), (I-b), (I-c)) or (II) or a pharmaceutically acceptable salt thereof), and a pharmaceutically acceptable excipient) can be used to treat a subject with conditions associated with excessive neuronal excitability, for example, epilepsy and other encephalopathies (e.g., epilepsy of infancy with migrating focal seizures (EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, and Lennox Gastaut syndrome, seizures) or cardiac dysfunctions (e.g., cardiac arrhythmia, Brugada syndrome, myocardial infarction), regardless of whether or not the disease or disorder is associated with a gain-of-function mutation in KCNT1.

Pharmaceutical Compositions and Routes of Administration

Compounds provided in accordance with the present invention, e.g., a compound of Formula (I), (e.g., (I-a), (I-b), (I-c)) or (II) or a pharmaceutically acceptable salt thereof, are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In some embodiments, a pharmaceutical composition comprising a disclosed compound, or pharmaceutically acceptable salt thereof, and a pharmaceutically acceptable carrier.

Enumerated Embodiments

The following enumerated embodiments are representative of some aspects of the invention.

1. A pharmaceutical composition comprising a compound of Formula I:

(I)

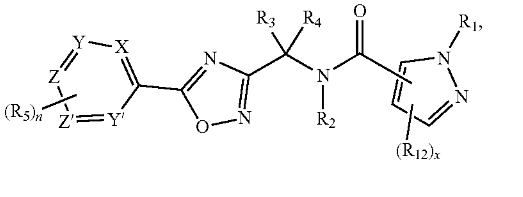

or a pharmaceutically acceptable salt thereof, wherein

X, Y, Z, Y', and Z' are each independently selected from CH and N, wherein the hydrogen of CH may be substituted with $R_5$, wherein at least 3 selected from X, Y, Z, Y', and Z' are CH;

$R_1$ is selected from the group consisting of $C_{1-6}$alkyl, $C_{3-10}$cycloalkyl, 3-10 membered heterocyclyl, 3-10 membered heteroaryl, and phenyl, wherein $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, C(O)N$(R_9)_2$, N$(R_9)_2$, $C_{3-7}$cycloalkyl, phenyl, 3-10 membered heteroaryl, and $C_{1-6}$alkoxy;

$R_{12}$ is selected from the group consisting of $C_{1-6}$alkyl, $C_{3-10}$cycloalkyl, 3-10 membered heterocyclyl, 3-10 membered heteroaryl, and phenyl, wherein the $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, —OH, —CN, $C_{1-6}$alkyl, $C_{1-6}$haloalkyl, and $C_{1-6}$alkoxy; or two $R_{12}$ on adjacent carbons can be taken together with the two carbons where $R_{12}$ are attached to form a carbocyclic ring;

x is 0, 1 or 2;

$R_2$ is hydrogen or $C_{1-4}$alkyl;

$R_3$ is selected from the group consisting of hydrogen, $C_{1-6}$alkyl, $C_{3-10}$ cycloalkyl, 3-10 membered heterocyclyl, 3-10 membered heteroaryl, and phenyl; and $R_4$ is selected from $C_{1-6}$alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$ cycloalkyl, 3-10 membered heterocyclyl, 3-10 membered heteroaryl, phenyl, $C_{3-7}$cycloalkylene, or 3-7 membered heterocyclene may be optionally substituted with one or more $R_7$;

each $R_5$ is independently selected from the group consisting of halogen, $C_{1-6}$alkyl, $C_{1-6}$haloalkyl, $C_{1-6}$alkylene-N$(R_9)_2$, $C_{1-6}$alkylene-O—$C_{3-10}$cycloalkyl, $C_{1-6}$alkoxy, $C_{1-6}$alkoxy substituted with $C_{3-10}$cycloalkyl optionally substituted with one or more halogens, $C_{1-6}$haloalkoxy, 3-10 membered heterocyclyl optionally substituted with one or more halogens or $C_{1-6}$alkoxy, 3-10 membered heteroaryl, $C_{1-6}$alkylene-OH, $C_{1-6}$alkylene-$C_{1-6}$ alkoxy, OH, N$(R_9)_2$, —C(O)O$R_8$, C(O)N$(R_9)_2$, $C_{1-6}$alkylene-CN, —CN, —S$(O)_2$—$C_{1-6}$alkyl, $C_{1-6}$alkylene-S$(O)_2$—$C_{1-6}$alkyl, —S$(O)_2$—N$(R_9)_2$, —OC(O)$C_{1-6}$alkyl, —O—$C_{3-10}$cycloalkyl optionally substituted with one or more halogen or $C_{1-6}$alkyl, and $C_{3-10}$cycloalkyl optionally substituted with one or more substituents selected from halogen, $C_{1-6}$alkyl, and $C_{1-6}$alkoxy;

n is selected from the group consisting of 0, 1, 2, and 3;

$R_7$ is each independently selected from the group consisting of phenyl, $C_{1-6}$alkoxy, —OH, —N$(R_9)_2$, —N$R_9$—S$O_2$—$C_{1-6}$alkyl, —O—($C_{1-6}$alkylene)-phenyl, $C_{3-10}$cycloalkyl, —C(O)O$R_8$, —C(O)N$(R_9)_2$, —N$R_{10}$C(O)—$R_{11}$, —CN, —S$(O)_2$—$C_{1-6}$alkyl, —S$(O)_2$—N$(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —N$(R_9)_2$;

$R_8$ is hydrogen or $C_{1-6}$alkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents each independently selected from halogen and —OH;

each $R_{10}$ is independently hydrogen or $C_{1-6}$alkyl;

$R_{11}$ is selected from the group consisting of $C_{1-6}$alkyl, $C_{1-6}$alkoxy, and —O—($C_{1-6}$alkylene)-phenyl; and when $R_3$ and $R_4$ are both hydrogen, at least one selected from X, Y, Z, Y', and Z' is N;

and a pharmaceutically acceptable excipient.

2. The pharmaceutical composition of embodiment 1, wherein one of X, Y, Z, Y', and Z' is N and the other four are CH.

3. The pharmaceutical composition of embodiment 1, wherein the compound is a compound of Formula I-a:

(I-a)

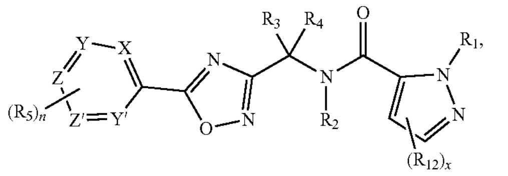

or a compound of Formula I-b:

(I-b)

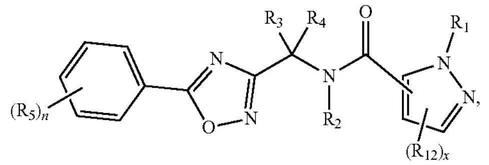

or a pharmaceutically acceptable salt thereof, wherein the variables are as defined in embodiment 1.

4. The pharmaceutical composition of embodiment 1, wherein the compound is a compound of Formula I-c:

(I-c)

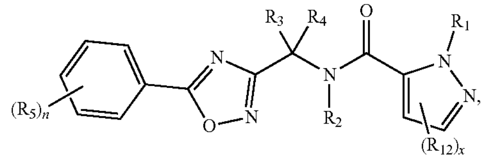

or a pharmaceutically acceptable salt thereof, wherein the variables are as defined in embodiment 1.

5. The pharmaceutical composition of any one of embodiments 1-4, wherein $R_2$ is hydrogen.

6. The pharmaceutical composition of any one of embodiments 1-4, wherein $R_2$ is methyl.

7. The pharmaceutical composition of any one of embodiments 1-6, wherein $R_3$ is hydrogen.

8. The pharmaceutical composition of any one of embodiments 1-6, wherein $R_3$ is $C_{1-6}$alkyl.

9. The pharmaceutical composition of any one of embodiments 1-6, wherein $R_3$ is selected from the group consisting of methyl, ethyl, and isopropyl.

10. The pharmaceutical composition of any one of embodiments 1-6, wherein $R_3$ is methyl.

11. The pharmaceutical composition of any one of embodiments 1-6, wherein $R_3$ is ethyl.

12. The pharmaceutical composition of any one of embodiments 1-6, wherein $R_3$ is $C_{1-6}$alkyl substituted with $C_{1-6}$alkoxy, —OH, or —C(O)$OR_8$.

13. The pharmaceutical composition of any one of embodiments 1-12, wherein $R_4$ is hydrogen.

14. The pharmaceutical composition of any one of embodiments 1-12, wherein $R_3$ and $R_4$ are taken together with the carbon attached to $R_3$ and $R_4$ to form a $C_{3-7}$cycloalkylene or 3-7 membered heterocyclene.

15. The pharmaceutical composition of embodiment 14, wherein the $C_{3-7}$cycloalkylene is selected from the group consisting of cyclopropyl, cyclobutyl, cyclopentyl, and cyclohexyl.

16. The pharmaceutical composition of embodiment 14, wherein the 3-7 membered heterocyclene is selected from the group consisting of oxetanyl, tetrahydrofuranyl, and tetrahydropyranyl.

17. The pharmaceutical composition of any one of embodiments 1-16, wherein each $R_5$ is independently selected from the group consisting of halogen, $C_{1-6}$alkyl, $C_{1-6}$haloalkyl, $C_{1-6}$alkoxy, $C_{1-6}$haloalkoxy, $C_{3-10}$cycloalkyl, O—$C_{3-10}$cycloalkyl, —OH, —CN, $N(R_9)_2$, and —C(O)$OR_8$.

18. The pharmaceutical composition of any one of embodiments 1-16, wherein each $R_5$ is methyl.

19. The pharmaceutical composition of any one of embodiments 1-16, wherein each $R_5$ is halogen.

20. The pharmaceutical composition of any one of embodiments 1-16, wherein each $R_5$ is —F.

21. The pharmaceutical composition of any one of embodiments 1-16, wherein each $R_5$ is —Cl.

22. The pharmaceutical composition of any one of embodiments 1-16, wherein each $R_5$ is methoxy.

23. The pharmaceutical composition of any one of embodiments 1-16, wherein each $R_5$ is —$CF_3$.

24. The pharmaceutical composition of any one of embodiments 1-16, wherein each $R_5$ is —$CHF_2$.

25. The pharmaceutical composition of any one of embodiments 1-16, wherein each $R_5$ is —C(O)$OR_8$.

26. The pharmaceutical composition of any one of embodiments 1-16, wherein each $R_5$ is cyclopropyl, cyclobutyl, or cyclopentyl.

27. The pharmaceutical composition of any one of embodiments 1-26, wherein n is 1.

28. The pharmaceutical composition of any one of embodiments 1-26, wherein n is 2.

29. The pharmaceutical composition of any one of embodiments 1-26, wherein n is 1 and $R_5$ is at the meta-position.

30. The pharmaceutical composition of any one of embodiments 1-26, wherein n is 2 and the two $R_5$ are at the ortho- and para- positions.

31. The pharmaceutical composition of any one of embodiments 1-26, wherein n is 2 and the two $R_5$ are at the meta- and para- positions.

32. The pharmaceutical composition of any one of embodiments 1-26, wherein n is 2 and the two $R_5$ are at the meta-positions.

33. The pharmaceutical composition of any one of embodiments 1-32, wherein $R_1$ is selected from the group consisting of $C_{1-6}$alkyl optionally substituted with $C_{1-6}$alkoxy, $N(R_9)_2$, C(O)$N(R_9)_2$, $C_{3-7}$cycloalkyl, pyridyl, tetrahydropyranyl, or phenyl, $C_{1-6}$haloalkyl, $C_{3-7}$cycloalkyl, phenyl optionally substituted with halogen, and pyridyl optionally substituted with halogen.

34. The pharmaceutical composition of any one of embodiments 1-32, wherein $R_1$ is $C_{1-6}$alkyl.

35. The pharmaceutical composition of any one of embodiments 1-32, wherein $R_1$ is methyl.

36. The pharmaceutical composition of any one of embodiments 1-32, wherein $R_1$ is ethyl.

37. The pharmaceutical composition of any one of embodiments 1-32, wherein $R_1$ is $C_{1-6}$haloalkyl.
38. The pharmaceutical composition of any one of embodiments 1-32, wherein $R_1$ is —$CH_2$—$CHF_2$.
39. The pharmaceutical composition of any one of embodiments 1-32, wherein $R_1$ is —$CHF_2$.
40. The pharmaceutical composition of any one of embodiments 1-32, wherein $R_1$ is $C_{3-7}$cycloalkyl.
41. The pharmaceutical composition of any one of embodiments 1-32, wherein $R_1$ is cyclopropyl.
42. The pharmaceutical composition of any one of embodiments 1-32, wherein $R_1$ is cyclobutyl.
43. The pharmaceutical composition of any one of embodiments 1-32, wherein $R_1$ is $C_{1-6}$alkyl substituted with $C_{1-6}$alkoxy.
44. The pharmaceutical composition of any one of embodiments 1-32, wherein $R_1$ is $C_{1-6}$alkyl substituted with methoxy.
45. The pharmaceutical composition of any one of embodiments 1-32, wherein $R_1$ is $C_{1-6}$alkyl substituted with $C_{3-7}$cycloalkyl.
46. The pharmaceutical composition of any one of embodiments 1-32, wherein $R_1$ is $C_{1-6}$alkyl substituted with cyclopropyl.
47. The pharmaceutical composition of any one of embodiments 1-32, wherein $R_1$ is phenyl substituted with halogen.
48. The pharmaceutical composition of any one of embodiments 1-47, wherein $R_{12}$ is selected from the group consisting of $C_{1-6}$alkyl, $C_{1-6}$haloalkyl, $C_{3-7}$cycloalkyl, and phenyl optionally substituted with halogen.
49. The pharmaceutical composition of any one of embodiments 1-47, wherein $R_{12}$ is $C_{3-7}$cycloalkyl.
50. The pharmaceutical composition of any one of embodiments 1-47, wherein $R_{12}$ is cyclopropyl.
51. The pharmaceutical composition of any one of embodiments 1-47, wherein $R_{12}$ is $C_{1-6}$alkyl.
52. The pharmaceutical composition of any one of embodiments 1-47, wherein $R_{12}$ is ethyl.
53. The pharmaceutical composition of any one of embodiments 1-47, wherein $R_{12}$ is methyl.
54. The pharmaceutical composition of any one of embodiments 1-47, wherein $R_{12}$ is t-butyl.
55. The pharmaceutical composition of any one of embodiments 1-47, wherein $R_{12}$ is isopropyl.
56. The pharmaceutical composition of any one of embodiments 1-47, wherein $R_{12}$ is $C_{1-6}$haloalkyl.
57. The pharmaceutical composition of any one of embodiments 1-47, wherein $R_{12}$ is —$CF_3$.
58. The pharmaceutical composition of any one of embodiments 1-47, wherein $R_{12}$ is —$CHF_2$.
59. The pharmaceutical composition of any one of embodiments 1-47, wherein $R_{12}$ is phenyl optionally substituted with —F.
60. The pharmaceutical composition of any one of embodiments 1-59, wherein x is 1.
61. The pharmaceutical composition of any one of embodiments 1-59, wherein x is 2.
62. A compound of Formula II.

(II)

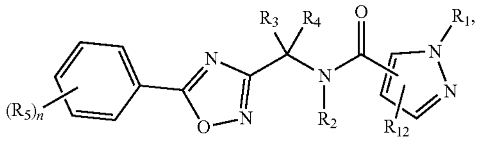

or a pharmaceutically acceptable salt thereof, wherein $R_1$ is $C_{1-6}$alkyl or $C_{3-7}$cycloalkyl, wherein the $C_{1-6}$alkyl or $C_{3-7}$cycloalkyl is optionally substituted with one or more substituents independently selected from halogen and $C_{1-6}$alkoxy;

$R_{12}$ is $C_{1-6}$alkyl optionally substituted with one or more halogen or $C_{1-6}$alkoxy;

$R_2$ is hydrogen or $C_{1-4}$alkyl;

$R_3$ is selected from the group consisting of $C_{1-6}$alkyl, $C_{3-10}$ cycloalkyl, 3-10 membered heterocyclyl, 3-10 membered heteroaryl, and phenyl; and $R_4$ is selected from $C_{1-6}$alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$ cycloalkyl, 3-10 membered heterocyclyl, 3-10 membered heteroaryl, phenyl, $C_{3-7}$cycloalkylene or 3-7 membered heterocyclene may be optionally substituted with $R_7$;

$R_5$ is selected from the group consisting of halogen, $C_{1-6}$alkyl, $C_{1-6}$alkoxy, $C_{1-6}$haloalkyl, $C_{1-6}$haloalkoxy, 3-10 membered heterocyclyl, 3-10 membered heteroaryl, —$C_{1-6}$alkylene-OH, OH, —C(O)$OR_8$, —C(O)$N(R_9)_2$, —$C_{1-6}$alkylene-CN, —CN, —$S(O)_2$—$C_{1-6}$alkyl, $C_{1-6}$alkylene-$S(O)_2$—$C_{1-6}$alkyl, —$S(O)_2$—$N(R_9)_2$, —OC(O)$C_{1-6}$alkyl, and —O—$C_{3-10}$cycloalkyl optionally substituted with one or more halogen;

$R_7$ is each independently selected from the group consisting of phenyl, $C_{1-6}$alkoxy, —OH, —O—($C_{1-6}$alkylene)-phenyl, $C_{3-10}$cycloalkyl, —C(O)$OR_8$, —C(O)$N(R_9)_2$, —$NR_{10}$C(O)—$R_{11}$, —CN, —$S(O)_2$—$C_{1-6}$ alkyl, —$S(O)_2$—$N(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —$N(R_9)_2$;

$R_8$ is hydrogen or $C_{1-6}$alkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents selected from halogen and —OH;

each $R_{10}$ is independently hydrogen or $C_{1-6}$alkyl;

$R_{11}$ is selected from the group consisting of $C_{1-6}$alkyl, $C_{1-6}$alkoxy, and —O—($C_{1-6}$alkylene)-phenyl; and n is selected from the group consisting of 0, 1, 2, and 3.

63. The compound of embodiment 62, wherein $R_2$ is hydrogen.
64. The compound of embodiment 62 or 63, wherein $R_3$ is $C_{1-6}$alkyl.
65. The compound of any one of embodiments 62-64, wherein $R_3$ is methyl.
66. The compound of any one of embodiments 62-64, wherein $R_3$ is ethyl.
67. The compound of embodiment 62 or 63, wherein $R_3$ is $C_{1-6}$alkyl substituted with $C_{1-6}$alkoxy.
68. The compound of any one of embodiments 62-67, wherein $R_4$ is hydrogen.
69. The compound of any one of embodiments 62-67, wherein $R_3$ and $R_4$ are taken together with the carbon attached to $R_3$ and $R_4$ to form a $C_{3-7}$cycloalkylene or 3-7 membered heterocyclene.
70. The compound of any one of embodiments 62-69, wherein each $R_5$ is methyl.

71. The compound of any one of embodiments 62-69, wherein each $R_5$ is halogen.

72. The compound of any one of embodiments 62-69, wherein each $R_5$ is —F.

73. The compound of any one of embodiments 62-69, wherein each $R_5$ is —Cl.

74. The compound of any one of embodiments 62-69, wherein each $R_5$ is methoxy.

75. The compound of any one of embodiments 62-69, wherein each $R_5$ is $—CF_3$.

76. The compound of any one of embodiments 62-69, wherein each $R_5$ is $—CHF_2$.

77. The compound of any one of embodiments 62-69, wherein each $R_5$ is $—C(O)OR_8$.

78. The compound of any one of embodiments 62-77, wherein n is 1.

79. The compound of any one of embodiments 62-77, wherein n is 2.

80. The compound of any one of embodiments 62-77, wherein n is 1 and $R_5$ is at the meta-position.

81. The compound of any one of embodiments 62-77, wherein n is 2 and the two $R_5$ are at the ortho- and para-positions.

82. The compound of any one of embodiments 62-77, wherein n is 2 and the two $R_5$ are at the meta- and para-positions.

83. The compound of any one of embodiments 62-77, wherein n is 2 and the two $R_5$ are at the meta-positions.

84. The compound of any one of embodiments 62-83, wherein $R_1$ is $C_{1-6}$alkyl.

85. The compound of any one of embodiments 62-83, wherein $R_1$ is methyl.

86. The compound of any one of embodiments 62-83, wherein $R_1$ is ethyl.

87. The compound of any one of embodiments 62-83, wherein $R_1$ is $C_{1-6}$haloalkyl.

88. The compound of any one of embodiments 62-83, wherein $R_1$ is $—CH_2—CHF_2$.

89. The compound of any one of embodiments 62-83, wherein $R_1$ is $—CHF_2$.

90. The compound of any one of embodiments 62-83, wherein $R_1$ is $C_{3-7}$cycloalkyl.

91. The compound of any one of embodiments 62-83, wherein $R_1$ is cyclopropyl.

92. The compound of any one of embodiments 62-91, wherein $R_{12}$ is $C_{1-6}$alkyl.

93. The compound of any one of embodiments 62-91, wherein $R_{12}$ is ethyl.

94. The compound of any one of embodiments 62-91, wherein $R_{12}$ is methyl.

95. The compound of any one of embodiments 62-91, wherein $R_{12}$ is t-butyl.

96. The compound of any one of embodiments 62-91, wherein $R_{12}$ is $C_{1-6}$haloalkyl.

97. The compound of any one of embodiments 62-91, wherein $R_{12}$ is $—CF_3$.

98. The compound of any one of embodiments 62-91, wherein $R_{12}$ is $—CHF_2$.

99. A method of treating a neurological disease or disorder, wherein the method comprises administering to a subject in need thereof a compound of Formula I.

(I)

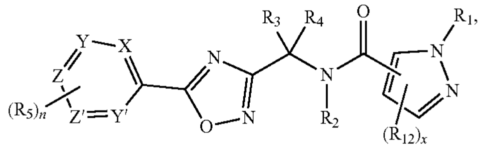

or a pharmaceutically acceptable salt thereof, wherein

X, Y, Z, Y', and Z' are each independently selected from CH and N, wherein the hydrogen of CH may be substituted with $R_5$, wherein at least 3 selected from X, Y, Z, Y', and Z' are CH;

$R_1$ is selected from the group consisting of $C_{1-6}$alkyl, $C_{3-10}$cycloalkyl, 3-10 membered heterocyclyl, 3-10 membered heteroaryl, and phenyl, wherein $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, $C(O)N(R_9)_2$, $N(R_9)_2$, $C_{3-7}$cycloalkyl, phenyl, 3-10 membered heteroaryl, and $C_{1-6}$alkoxy;

$R_{12}$ is selected from the group consisting of $C_{1-6}$alkyl, $C_{3-10}$cycloalkyl, 3-10 membered heterocyclyl, 3-10 membered heteroaryl, and phenyl, wherein the $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, —OH, —CN, $C_{1-6}$alkyl, $C_{1-6}$haloalkyl, and $C_{1-6}$alkoxy; or two $R_{12}$ on adjacent carbons can be taken together with the two carbons where $R_{12}$ are attached to form a carbocyclic ring;

x is 0, 1 or 2;

$R_2$ is hydrogen or $C_{1-4}$alkyl;

$R_3$ is selected from the group consisting of hydrogen, $C_{1-6}$alkyl, $C_{3-10}$ cycloalkyl, 3-10 membered heterocyclyl, 3-10 membered heteroaryl, and phenyl; and $R_4$ is selected from $C_{1-6}$alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$cycloalkyl, 3-10 membered heterocyclyl, 3-10 membered heteroaryl, phenyl, $C_{3-7}$cycloalkylene, or 3-7 membered heterocyclene may be optionally substituted with one or more $R_7$;

each $R_5$ is independently selected from the group consisting of halogen, $C_{1-6}$alkyl, $C_{1-6}$haloalkyl, $C_{1-6}$alkylene-$N(R_9)_2$, $C_{1-6}$alkylene-O—$C_{3-10}$cycloalkyl, $C_{1-6}$alkoxy, $C_{1-6}$alkoxy substituted with $C_{3-10}$cycloalkyl optionally substituted with one or more halogens, $C_{1-6}$haloalkoxy, 3-10 membered heterocyclyl optionally substituted with one or more halogens or $C_{1-6}$alkoxy, 3-10 membered heteroaryl, $C_{1-6}$alkylene-OH, $C_{1-6}$alkylene-$C_{1-6}$ alkoxy, OH, $N(R_9)_2$, $—C(O)OR_8$, $C(O)N(R_9)_2$, $C_{1-6}$alkylene-CN, —CN, $—S(O)_2—C_{1-6}$alkyl, $C_{1-6}$alkylene-$S(O)_2—C_{1-6}$alkyl, $—S(O)_2—N(R_9)_2$, $—OC(O)C_{1-6}$alkyl, —O—$C_{3-10}$cycloalkyl optionally substituted with one or more halogen or $C_{1-6}$alkyl, and $C_{3-10}$cycloalkyl optionally substituted with one or more substituents selected from halogen, $C_{1-6}$alkyl, and $C_{1-6}$alkoxy;

n is selected from the group consisting of 0, 1, 2, and 3;

$R_7$ is each independently selected from the group consisting of phenyl, $C_{1-6}$alkoxy, —OH, $—N(R_9)_2$, $—NR_9—$ $SO_2$—$C_{1-6}$alkyl, —O—($C_{1-6}$alkylene)-phenyl, $C_{3-10}$cycloalkyl, —C(O)O$R_8$, —C(O)N$(R_9)_2$, —N$R_{10}$C(O)—$R_{11}$, —CN, —S$(O)_2$—$C_{1-6}$alkyl, —S$(O)_2$—N$(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —N$(R_9)_2$;

$R_8$ is hydrogen or $C_{1-6}$alkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents each independently selected from halogen and —OH;

each $R_{10}$ is independently hydrogen or $C_{1-6}$alkyl;

$R_{11}$ is selected from the group consisting of $C_{1-6}$alkyl, $C_{1-6}$alkoxy, and —O—($C_{1-6}$alkylene)-phenyl; and when $R_3$ and $R_4$ are both hydrogen, at least one selected from X, Y, Z, Y', and Z' is N.

100. A method of treating a disease or condition associated with excessive neuronal excitability, wherein the method comprises administering to a subject in need thereof a compound of Formula I:

(I)

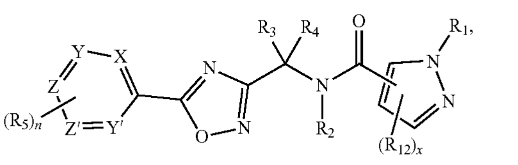

or a pharmaceutically acceptable salt thereof, wherein

X, Y, Z, Y', and Z' are each independently selected from CH and N, wherein the hydrogen of CH may be substituted with $R_5$, wherein at least 3 selected from X, Y, Z, Y', and Z' are CH;

$R_1$ is selected from the group consisting of $C_{1-6}$alkyl, $C_{3-10}$cycloalkyl, 3-10 membered heterocyclyl, 3-10 membered heteroaryl, and phenyl, wherein $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, C(O)N$(R_9)_2$, N$(R_9)_2$, $C_{3-7}$cycloalkyl, phenyl, 3-10 membered heteroaryl, and $C_{1-6}$alkoxy;

$R_{12}$ is selected from the group consisting of $C_{1-6}$alkyl, $C_{3-10}$cycloalkyl, 3-10 membered heterocyclyl, 3-10 membered heteroaryl, and phenyl, wherein the $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, —OH, —CN, $C_{1-6}$alkyl, $C_{1-6}$haloalkyl, and $C_{1-6}$alkoxy; or two $R_{12}$ on adjacent carbons can be taken together with the two carbons where $R_{12}$ are attached to form a carbocyclic ring;

x is 0, 1 or 2;

$R_2$ is hydrogen or $C_{1-4}$alkyl;

$R_3$ is selected from the group consisting of hydrogen, $C_{1-6}$alkyl, $C_{3-10}$ cycloalkyl, 3-10 membered heterocyclyl, 3-10 membered heteroaryl, and phenyl; and $R_4$ is selected from $C_{1-6}$alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$ cycloalkyl, 3-10 membered heterocyclyl, 3-10 membered heteroaryl, phenyl, $C_{3-7}$cycloalkylene, or 3-7 membered heterocyclene may be optionally substituted with one or more $R_7$;

each $R_5$ is independently selected from the group consisting of halogen, $C_{1-6}$alkyl, $C_{1-6}$haloalkyl, $C_{1-6}$alkylene-N$(R_9)_2$, $C_{1-6}$alkylene-O—$C_{3-10}$cycloalkyl, $C_{1-6}$alkoxy, $C_{1-6}$alkoxy substituted with $C_{3-10}$cycloalkyl optionally substituted with one or more halogens, $C_{1-6}$haloalkoxy, 3-10 membered heterocyclyl optionally substituted with one or more halogens or $C_{1-6}$alkoxy, 3-10 membered heteroaryl, $C_{1-6}$alkylene-OH, $C_{1-6}$alkylene-$C_{1-6}$ alkoxy, OH, N$(R_9)_2$, —C(O)O$R_8$, C(O)N$(R_9)_2$, $C_{1-6}$alkylene-CN, —CN, —S$(O)_2$—$C_{1-6}$alkyl, $C_{1-6}$alkylene-S$(O)_2$—$C_{1-6}$alkyl, —S$(O)_2$—N$(R_9)_2$, —OC(O)$C_{1-6}$alkyl, —O—$C_{3-10}$cycloalkyl optionally substituted with one or more halogen or $C_{1-6}$alkyl, and $C_{3-10}$cycloalkyl optionally substituted with one or more substituents selected from halogen, $C_{1-6}$alkyl, and $C_{1-6}$alkoxy;

n is selected from the group consisting of 0, 1, 2, and 3;

$R_7$ is each independently selected from the group consisting of phenyl, $C_{1-6}$alkoxy, —OH, —N$(R_9)_2$, —N$R_9$—$SO_2$—$C_{1-6}$alkyl, —O—($C_{1-6}$alkylene)-phenyl, $C_{3-10}$cycloalkyl, —C(O)O$R_8$, —C(O)N$(R_9)_2$, —N$R_{10}$C(O)—$R_{11}$, —CN, —S$(O)_2$—$C_{1-6}$alkyl, —S$(O)_2$—N$(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —N$(R_9)_2$;

$R_8$ is hydrogen or $C_{1-6}$alkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents each independently selected from halogen and —OH;

each $R_{10}$ is independently hydrogen or $C_{1-6}$alkyl;

$R_{11}$ is selected from the group consisting of $C_{1-6}$alkyl, $C_{1-6}$alkoxy, and —O—($C_{1-6}$alkylene)-phenyl; and when $R_3$ and $R_4$ are both hydrogen, at least one selected from X, Y, Z, Y', and Z' is N.

101. A method of treating a disease or condition associated with a gain-of-function mutation of a gene (e.g., KCNT1), wherein the method comprises administering to a subject in need thereof a compound of Formula I:

(I)

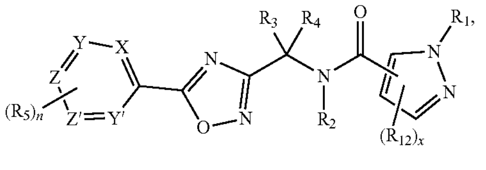

or a pharmaceutically acceptable salt thereof, wherein

X, Y, Z, Y', and Z' are each independently selected from CH and N, wherein the hydrogen of CH may be substituted with $R_5$, wherein at least 3 selected from X, Y, Z, Y', and Z' are CH;

$R_1$ is selected from the group consisting of $C_{1-6}$alkyl, $C_{3-10}$cycloalkyl, 3-10 membered heterocyclyl, 3-10 membered heteroaryl, and phenyl, wherein $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, C(O)N$(R_9)_2$, $N(R_9)_2$, $C_{3-7}$cycloalkyl, phenyl, 3-10 membered heteroaryl, and $C_{1-6}$alkoxy;

$R_{12}$ is selected from the group consisting of $C_{1-6}$alkyl, $C_{3-10}$cycloalkyl, 3-10 membered heterocyclyl, 3-10 membered heteroaryl, and phenyl, wherein the $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, —OH, —CN, $C_{1-6}$alkyl, $C_{1-6}$haloalkyl, and $C_{1-6}$alkoxy; or two $R_{12}$ on adjacent carbons can be taken together with the two carbons where $R_{12}$ are attached to form a carbocyclic ring;

x is 0, 1 or 2;

$R_2$ is hydrogen or $C_{1-4}$alkyl;

$R_3$ is selected from the group consisting of hydrogen, $C_{1-6}$alkyl, $C_{3-10}$ cycloalkyl, 3-10 membered heterocyclyl, 3-10 membered heteroaryl, and phenyl; and $R_4$ is selected from $C_{1-6}$alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$cycloalkyl, 3-10 membered heterocyclyl, 3-10 membered heteroaryl, phenyl, $C_{3-7}$cycloalkylene, or 3-7 membered heterocyclene may be optionally substituted with one or more $R_7$;

each $R_5$ is independently selected from the group consisting of halogen, $C_{1-6}$alkyl, $C_{1-6}$haloalkyl, $C_{1-6}$alkylene-$N(R_9)_2$, $C_{1-6}$alkylene-O—$C_{3-10}$cycloalkyl, $C_{1-6}$alkoxy, $C_{1-6}$alkoxy substituted with $C_{3-10}$cycloalkyl optionally substituted with one or more halogens, $C_{1-6}$haloalkoxy, 3-10 membered heterocyclyl optionally substituted with one or more halogens or $C_{1-6}$alkoxy, 3-10 membered heteroaryl, $C_{1-6}$alkylene-OH, $C_{1-6}$alkylene-$C_{1-6}$ alkoxy, OH, $N(R_9)_2$, —C(O)$OR_8$, C(O)$N(R_9)_2$, $C_{1-6}$alkylene-CN, —CN, —$S(O)_2$—$C_{1-6}$alkyl, $C_{1-6}$alkylene-$S(O)_2$—$C_{1-6}$alkyl, —$S(O)_2$—$N(R_9)_2$, —OC(O)$C_{1-6}$alkyl, —O—$C_{3-10}$cycloalkyl optionally substituted with one or more halogen or $C_{1-6}$alkyl, and $C_{3-10}$cycloalkyl optionally substituted with one or more substituents selected from halogen, $C_{1-6}$alkyl, and $C_{1-6}$alkoxy;

n is selected from the group consisting of 0, 1, 2, and 3;

$R_7$ is each independently selected from the group consisting of phenyl, $C_{1-6}$alkoxy, —OH, —$N(R_9)_2$, —$NR_9$—$SO_2$—$C_{1-6}$alkyl, —O—($C_{1-6}$alkylene)-phenyl, $C_{3-10}$cycloalkyl, —C(O)$OR_8$, —C(O)$N(R_9)_2$, —$NR_{10}$C(O)—$R_{11}$, —CN, —$S(O)_2$—$C_{1-6}$alkyl, —$S(O)_2$—$N(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —$N(R_9)_2$;

$R_8$ is hydrogen or $C_{1-6}$alkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents each independently selected from halogen and —OH;

each $R_{10}$ is independently hydrogen or $C_{1-6}$alkyl;

$R_1$ is selected from the group consisting of $C_{1-6}$alkyl, $C_{1-6}$alkoxy, and —O—($C_{1-6}$alkylene)-phenyl; and when $R_3$ and $R_4$ are both hydrogen, at least one selected from X, Y, Z, Y', and Z' is N.

102. A method of treating a neurological disease or disorder, wherein the method comprises administering to a subject in need thereof a compound of any one of embodiments 62-98 or a pharmaceutical composition of any one of embodiments 1-61.

103. A method of treating a disease or condition associated with excessive neuronal excitability, wherein the method comprises administering to a subject in need thereof a compound of any one of embodiments 62-98 or a pharmaceutical composition of any one of embodiments 1-61.

104. A method of treating a disease or condition associated with a gain-of-function mutation of a gene (e.g., KCNT1), wherein the method comprises administering to a subject in need thereof a compound of any one of embodiments 62-98 or a pharmaceutical composition of any one of embodiments 1-61.

105. The method of any one of embodiments 99-104, wherein the neurological disease or disorder, the disease or condition associated with excessive neuronal excitability, or the disease or condition associated with a gain-of-function mutation of a gene (e.g., KCNT1) is epilepsy, an epilepsy syndrome, or an encephalopathy.

106. The method of any one of embodiments 99-104, wherein the neurological disease or disorder, the disease or condition associated with excessive neuronal excitability, or the disease or condition associated with a gain-of-function mutation of a gene (e.g., KCNT1) is a genetic or pediatric epilepsy or a genetic or pediatric epilepsy syndrome.

107. The method of any one of embodiments 99-104, wherein the neurological disease or disorder, the disease or condition associated with excessive neuronal excitability, or the disease or condition associated with a gain-of-function mutation of a gene (e.g., KCNT1) is a cardiac dysfunction.

108. The method of any one of embodiments 99-104, wherein the neurological disease or disorder, the disease or condition associated with excessive neuronal excitability, or the disease or condition associated with a gain-of-function mutation of a gene (e.g., KCNT1) is selected from the group consisting of epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, Lennox Gastaut syndrome, seizures (e.g., Generalized tonic clonic seizures, Asymmetric Tonic Seizures), leukodystrophy, leukoencephalopathy, intellectual disability, Multifocal Epilepsy, Drug resistant epilepsy, Temporal lobe epilepsy, or cerebellar ataxia).

109. The method of any one of embodiments 99-104, wherein the neurological disease or disorder, the disease or condition associated with excessive neuronal excitability, or the disease or condition associated with a gain-of-function mutation of a gene (e.g., KCNT1) is selected from the group consisting of cardiac arrhythmia, sudden unexpected death in epilepsy, Brugada syndrome, and myocardial infarction.

110. The method of any one of embodiments 99-104, wherein the neurological disease or disorder, the disease or condition associated with excessive neuronal excitability, or the disease or condition associated with a gain-of-function mutation of a gene (e.g., KCNT1) is selected from pain and related conditions (e.g. neuropathic pain, acute/chronic pain, migraine).

111. The method of any one of embodiments 99-104, the neurological disease or disorder, the disease or condition associated with excessive neuronal excitability, or the disease or condition associated with a gain-of-function mutation of a gene (e.g., KCNT1) is a muscle disorder (e.g. myotonia, neuromyotonia, cramp muscle spasms, spasticity).

112. The method of any one of embodiments 99-104, wherein the neurological disease or disorder, the disease or condition associated with excessive neuronal excitability, or the disease or condition associated with a gain-of-function mutation of a gene (e.g., KCNT1) is selected from itch and pruritis, ataxia and cerebellar ataxias.

113. The method of any one of embodiments 99-104, wherein the neurological disease or disorder, the disease or condition associated with excessive neuronal excitability, or the disease or condition associated with a gain-of-function mutation of a gene (e.g., KCNT1) is selected from psychiatric disorders (e.g. major depression, anxiety, bipolar disorder, schizophrenia).

114. The method of any one of embodiments 99-104, wherein the neurological disease or disorder or the disease or condition associated with excessive neuronal excitability and/or a gain-of-function mutation in a gene (e.g., KCNT1) is selected from the group consisting of learning disorders, Fragile X, neuronal plasticity, and autism spectrum disorders.

115. The method of any one of embodiments 99-104, wherein the neurological disease or disorder, the disease or condition associated with excessive neuronal excitability, or the disease or condition associated with a gain-of-function mutation of a gene (e.g., KCNT1) is selected from the group consisting of epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

List of Abbreviations

THF tetrahydrofuran
DMF N,N-dimethylformamide
EtOAc ethyl acetate
PE petroleum ether
DMSO dimethyl sulfoxide
HOBt hydroxybenzotriazole
DMAP 4-dimethylaminopyridine
DIPEA N,N-diisopropylethylamine
HATU o-(7-azabenzotriazol-1-yl)-N,N,N',N'-tetramethyluronium hexafluorophosphate
EGTA ethylene glycol-bis(O-aminoethyl ether)-N,N,N',N-tetraacetic acid
NMDG N-methyl-D-glucamine
HEPES 4-(2-hydroxyethyl)piperazine-1-ethanesulfonic acid
IC50 half maximal inhibitory concentration
LCMS liquid chromatography-mass spectrometry
HPLC high-performance liquid chromatography
SFC supercritical fluid chromatography
MS mass spectrometry
NMR nuclear magnetic resonance
TFAA trifluoroacetic anhydride
EDCI 1-ethyl-3-(3-dimethylaminopropyl)carbodiimide Example 1. Synthesis of 2-methyl-N-[1-[5-(m-tolyl)-1,2,4-oxadiazol-3-yl]ethyl]-5-(trifluoromethyl)pyrazole-3-carboxamide (Compound 1)

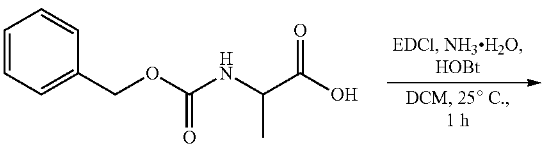

A1

-continued

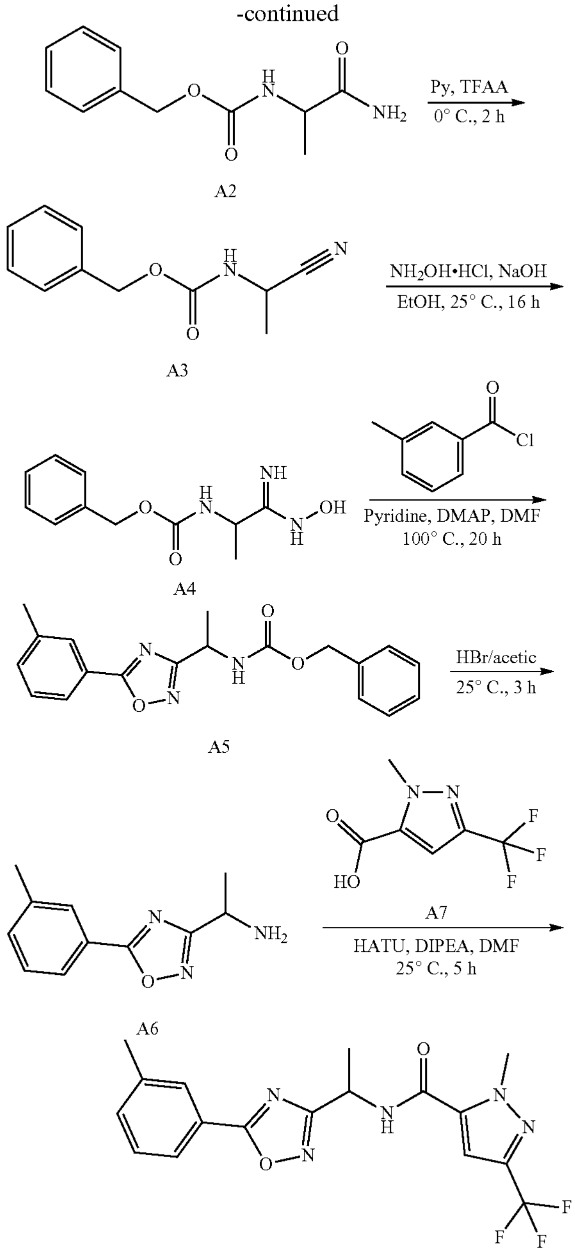

A2

A3

A4

A5

A7

A6

Compound 1

A2: benzyl N-(2-amino-1-methyl-2-oxo-ethyl)carbamate

To a mixture of 2-(benzyloxycarbonylamino)propanoic acid (A1) (2 g, 8.96 mmol) and HOBt (2.42 g, 17.92 mmol) in $CH_2Cl_2$ (15 mL) was added EDCI (3.44 g, 17.92 mmol) at 0° C., and the mixture was stirred at 25° C. for 30 minutes. Ammonia hydrate (1.73 mL, 44.8 mmol) was added to the mixture at 0° C., and the mixture was warmed to around 25° C. and stirred for about 30 minutes. The mixture was filtered through Celite and eluted with EtOAc (10 mL×2), and the filtrate was concentrated to give a residue. The residue was diluted with EtOAc (20 mL), filtered, washed with EtOAc (5 mL×2), and dried to give the product (730 mg, 3.28 mmol, 36% yield) as a solid. $^1H$ NMR (400 MHz, DMSO-$d_6$) $\delta_H$=7.42-7.23 (m, 7H), 6.95 (br s, 1H), 5.06-4.97 (m, 2H), 3.97 (quin, 1H), 1.20 (d, 3H). LCMS $R_t$=0.66 min in 1.5 min chromatography, 5-95AB, MS ESI calcd. for $C_{11}H_{15}N_2O_3$ $[M+H]^+$ 223.1, found 222.9.

A3: benzyl N-(1-cyanoethyl)carbamate

To a mixture of benzyl N-(2-amino-1-methyl-2-oxo-ethyl)carbamate (A2) (730 mg, 3.28 mmol) in THF (10 mL) pyridine was added (1.06 mL, 13.14 mmol) and trifluoroacetic anhydride (0.93 mL, 6.57 mmol) at around 0° C. The mixture was stirred at around 0° C. for about 2 h. The mixture was acidified with 1 N HCl to pH~3 and extracted with EtOAc (20 mL×2). The combined organic phase was washed with $NaHCO_3$ (30 mL), water (30 mL), and brine (30 mL), dried over $Na_2SO_4$, filtered, and concentrated to give crude A3 (600 mg, 2.61 mmol, 79% yield) as an oil. LCMS $R_t$=0.75 min in 1.5 min chromatography, 5-95AB, MS ESI calcd. for $C_{11}H_{13}N_2O_2$ $[M+H]^+$ 205.1, found 205.0.

A4: benzyl N-[2-(hydroxyamino)-2-imino-1-methyl-ethyl]carbamate

A mixture of benzyl N-(1-cyanoethyl)carbamate (A3) (600 mg, 2.94 mmol), $NH_2OH$—HCl (612.46 mg, 8.81 mmol) and NaOH (352.54 mg, 8.81 mmol) in ethanol (10 mL) was stirred at around 25° C. for about 16 h. The mixture was concentrated to remove most of EtOH, then diluted with $H_2O$ (20 mL), and extracted with EtOAc (20 mL×2). The combined organic phase was washed with brine (30 mL), dried over $Na_2SO_4$, filtered, and concentrated to give the crude product. The crude product was diluted with EtOAc (10 mL), filtered, washed with EtOAc (3 mL×2), and dried to give crude A4 (440 mg, 1.40 mmol, 47% yield) as a solid. $^1H$ NMR (400 MHz, DMSO-$d_6$) $\delta_H$=8.99 (s, 1H), 7.41-7.24 (m, 6H), 5.25 (br s, 2H), 5.05-4.97 (m, 2H), 4.14-4.04 (m, 1H), 1.22 (d, 3H). LCMS $R_t$=0.58 min in 1.5 min chromatography, 5-95AB, MS ESI calcd. for $C_{11}H_{16}N_3O_3$ $[M+H]^+$ 238.1, found 238.1.

A5: benzyl N-[1-[5-(m-tolyl)-1,2,4-oxadiazol-3-yl]ethyl]carbamate

A mixture of benzyl N-[2-(hydroxyamino)-2-imino-1-methyl-ethyl]carbamate (A4) (300 mg, 1.26 mmol), pyridine (1.73 mL, 21.5 mmol), 3-methylbenzoyl chloride (293.2 mg, 1.9 mmol), and DMAP (15.45 mg, 0.13 mmol) in DMF (8 mL) was stirred at around 25° C. for about 4 h, then heated to around 100° C. and stirred for about 16 h. After cooled to room temperature, the reaction was quenched with saturated aqueous $NH_4Cl$ (20 mL), and the mixture was extracted with EtOAc (20 mL×2). The combined organic phase was washed with brine (30 mL), dried over $Na_2SO_4$, filtered, and concentrated to give the crude product. The crude product was purified by flash column chromatography on silica gel (EtOAc in PE=0% to 30%) to give the A5 (640 mg, 1.17 mmol, 92% yield) as an oil. LCMS $R_t$=0.93 min in 1.5 min chromatography, 5-95AB, MS ESI calcd. for $C_{19}H_{20}N_3O_3$ $[M+H]^+$ 338.1, found 338.6.

A6: 1-[5-(m-tolyl)-1,2,4-oxadiazol-3-yl]ethanamine

A mixture of benzyl N-[1-[5-(m-tolyl)-1,2,4-oxadiazol-3-yl]ethyl]carbamate (A5) (250 mg, 0.74 mmol) in HBr/acetic acid (30 mL, 0.74 mmol) was stirred at around 25° C. for about 3 h. The mixture was basified with saturated aqueous $Na_2CO_3$ to pH~10, extracted with EtOAc (60 mL×2). The combined organic phase was washed with brine (100 mL), dried over $Na_2SO_4$, filtered, and concentrated to give the crude product. The crude product was triturated from EtOAc (3 mL) to give A6 (60 mg, 0.25 mmol, 33% yield) as a solid. LCMS $R_t$=0.66 min in 1.5 min chromatography, 5-95AB, MS ESI calcd. for $C_{11}H_{14}N_3O$ $[M+H]^+$ 204.1, found 204.1.

Compound 1: 2-methyl-N-[1-[5-(m-tolyl)-1,2,4-oxadiazol-3-yl]ethyl]-5-(trifluoromethyl)pyrazole-3-carboxamide A mixture of 2-methyl-5-(trifluoromethyl)pyrazole-3-carboxylic acid (A7) (68.77 mg, 0.35 mmol), HATU (224.5 mg, 0.59 mmol), DIPEA (0.12 mL, 0.89 mmol), and 1-[5-(m-tolyl)-1,2,4-oxadiazol-3-yl]ethanamine (A6) (60 mg, 0.30 mmol) in DMF (3 mL) was stirred at around 25° C. for about 5 h. The reaction was quenched with saturated aqueous $NH_4Cl$ (10 mL), and the mixture was extracted with EtOAc (20 mL×2). The combined organic phase was washed with brine (10 mL), dried over $Na_2SO_4$, filtered, and concentrated to give the product. The product was purified by flash column chromatography on silica gel (EtOAc in PE=0% to 50%), then triturated from n-hexane/DCM (2:1, 3 mL) to give the crude product. The crude product was purified by Prep-HPLC (Boston Prime C18 150 mm×30 mm 5 μm) A=$H_2O$ (0.05% $NH_4OH$) and B=$CH_3CN$; 44-74% B over 9 minutes) to give Compound 1 (16.06 mg, 42.3 μmol, 14% yield) as a solid. $^1H$ NMR (400 MHz, $CDCl_3$) $\delta_H$=7.98-7.90 (m, 2H), 7.44 (d, 2H), 6.89 (s, 1H), 6.69 (br d, 1H), 5.59-5.50 (m, 1H), 4.24 (s, 3H), 2.47 (s, 3H), 1.71 (d, 3H). LCMS $R_t$=1.29 min in 2.0 min chromatography, 10-80AB, MS ESI calcd. for $C_{17}H_{17}F_3N_5O_2$ $[M+H]^+$ 380.1, found 380.1.

Example 2: Synthesis of (S)—N-(1-(5-(2-cyclopropylpyridin-4-yl)-1,2,4-oxadiazol-3-yl)ethyl)-1-methyl-3-(trifluoromethyl)-1H-pyrazole-5-carboxamide (Compound 2a)

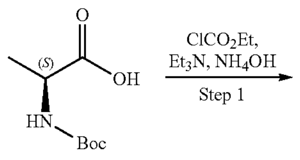

B1

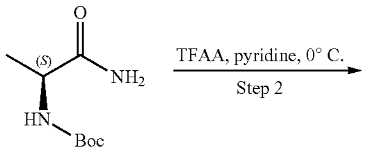

B2

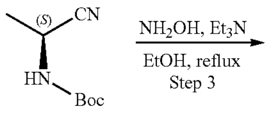

B3

-continued

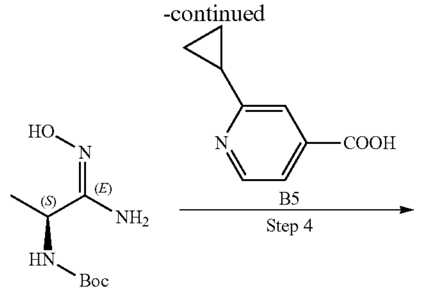

B4

B5

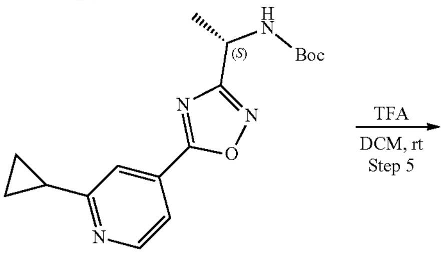

B6

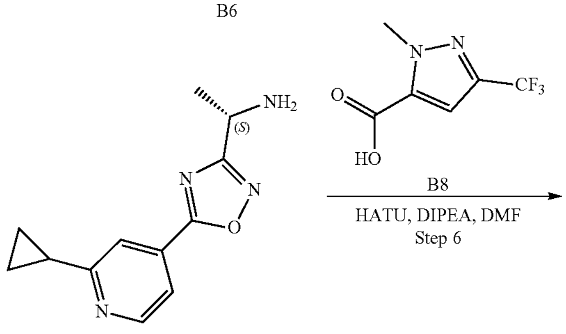

B7

B8

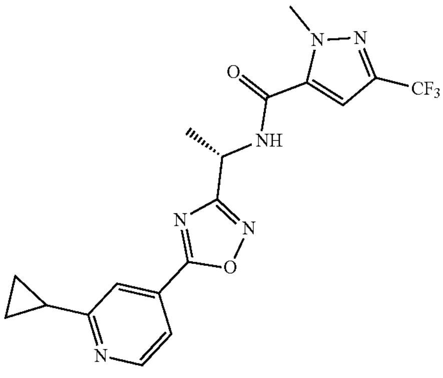

Compound 2a

B2: tert-butyl (S)-(1-amino-1-oxopropan-2-yl)carbamate

To a stirred solution of compound B1 (5 g, 26.43 mmol) and triethylamine (4.05 mL, 29.07 mmol) in THF (20 mL) was cooled to around −15° C. under a nitrogen atmosphere. To the resultant reaction mixture was added a solution of ethyl chloroformate (2.79 mL, 29.07 mmol) in THF (3 mL) drop wise at around the same temperature and stirred for about 25 minutes. Then ammonia solution (25%, 9.91 mL, 247.74 mmol) was added. The resultant reaction mixture was stirred at around 0° C. for about 3 h. After completion of reaction, the reaction mixture was concentrated under reduced pressure and acidified with aqueous solution of 1M $KHSO_4$ (pH=2-3). The aqueous layer was extracted with EtOAc (2×50 mL) and the combined organic layers were washed with 1 N $NaHCO_3$, water (10 mL), brine (10 mL) and dried over $Na_2SO_4$ and concentrated under reduced pressure to afford compound B2 (2.8 g, 14.88 mmol, 56% yield).

B3: tert-butyl (S)-(1-cyanoethyl)carbamate

To a stirred solution of compound B2 (2.8 g, 14.88 mmol) in pyridine (25 mL) was added trifluoroacetic anhydride (4.46 mL, 31.66 mmol) dropwise at around 0° C. and then stirring was continued at room temperature for about 3 h. After completion of the reaction, solvent was removed under reduced pressure. The obtained residue was dissolved in EtOAc (30 mL) and the organic layer was washed with 1 N $KHSO_4$, water (10 mL), brine (10 mL), dried over anhydrous $Na_2SO_4$ and concentrated under reduced pressure. The obtained crude residue was then purified by column chromatography to afford compound B3 (2.4 g, 14.1 mmol, 94% yield) as a liquid.

B4: tert-butyl (S,E)-(1-amino-1-(hydroxyimino) propan-2-yl)carbamate

To a stirred solution of compound B3 (2.4 g, 14.1 mmol) in EtOH (20 mL) was added $NH_2OH$—HCl (1.46 g, 21.15 mmol) followed by triethylamine (3.94 mL, 28.2 mmol) at room temperature and then stirring was continued at around 70° C. for about 3 h. After completion of reaction, the reaction mixture was concentrated under reduced pressure, diluted with water (20 mL) and extracted with EtOAc (2×30 mL). The combined organic layers were dried over anhydrous $Na_2SO_4$ and concentrated under reduced pressure to afford compound B4 (2 g, 9.8 mmol, 69% yield).

B6: tert-butyl (S)-(1-(5-(2-cyclopropylpyridin-4-yl)-1,2,4-oxadiazol-3-yl)ethyl)-carbamate To a stirred solution of compound B4 (2 g, 9.84 mmol) in 1,4-dioxane (20 mL) were added compound B5 (1.93 g, 11.81 mmol) and NN-dicyclohexylcarbodiimide (8.88 mL, 11.81 mmol) at room temperature and then stirring was continued at around 100° C. for about 16 h. After completion of reaction, the reaction mixture was concentrated under reduced pressure. The obtained crude residue was then purified by column chromatography using (0-70%) EtOAc in heptane to afford compound B6 (1.2 g, 3.64 mmol, 37% yield).

B7: (S)-1-(5-(2-cyclopropylpyridin-4-yl)-1,2,4-oxadiazol-3-yl)ethan-1-amine

To a stirred the solution of compound B6 (1 g, 3.03 mmol) in DCM (2 mL) was added 4 M HCl in dioxane (10 mL, 40 mmol) at around 0° C. and then stirring was continued at room temperature for about 2 h. After completion of the reaction, the reaction mixture was concentrated under reduced pressure to afford crude compound B7 (800 mg, 2.99 mmol, 99% yield) as an off-white solid.

Compound 2a: (S)—N-(1-(5-(2-cyclopropylpyridin-4-yl)-1,2,4-oxadiazol-3-yl)ethyl)-1-methyl-3-(trifluoromethyl)-1H-pyrazole-5-carboxamide To a stirred solution of compound B7 (354.9 mg, 1.33 mmol) and compound B8 (200 mg, 1.03 mmol) in DCM (10 mL) were added HATU (587.65 mg, 1.55 mmol) followed by DIPEA (0.54 mL, 3.09 mmol) at around 0° C. and then stirring was continued at room temperature for about 1 h. After completion of the reaction, the reaction mixture was quenched with water (10 mL) and extracted with DCM (2×25 mL). The combined organic layers were washed with water (20 mL), brine (20 mL), dried over anhydrous $Na_2SO_4$ and concentrated under reduced pressure. The obtained crude product was then purified by flash chromatography on silica gel using 0-90% EtOAc in n-heptane as an eluent followed by preparative HPLC to afford Compound 2a (98.55 mg, 0.24 mmol, 23% yield) as an off white solid. $^1H$ NMR (400 MHz, DMSO-$d_6$) δ 9.29 (d, J=7.5 Hz, 1H), 8.67 (d, J=5.0 Hz, 1H), 7.95 (s, 1H), 7.73 (dd, J=1.6, 5.1 Hz, 1H), 7.44 (s, 1H), 5.36 (quin, J=7.2 Hz, 1H), 4.14 (s, 3H), 2.42-2.23 (m, 1H), 1.62 (d, J=7.1 Hz, 3H), 1.06-0.96 (m, 4H). LCMS: 407.15 (M+H), Rt 1.972 min, 95.178%.

Example 3. Efficacy of Exemplary Compound in the Inhibition of KCNT1

KCNT1—Patch Clamp Assay

Inhibition of KCNT1 (KNa1.1, Slack) was evaluated using a tetracycline inducible cell line (HEK-TREX). Currents were recorded using the SyncroPatch 384PE automated, patch clamp system. Pulse generation and data collection were performed with PatchController384 V1.3.0 and DataController384 V1.2.1 (Nanion Technologies). The access resistance and apparent membrane capacitance were estimated using built-in protocols. Current were recorded in perforated patch mode (10 μM escin) from a population of cells. The cells were lifted, triturated, and resuspended at 800,000 cells/ml. The cells were allowed to recover in the cell hotel prior to experimentation. Currents were recorded at room temperature. The external solution contained the following (in mM): NaCl 105, NMDG 40, KCl 4, $MgCl_2$ 1, $CaCl_2$) 5 and HEPES 10 (pH=7.4, Osmolarity ~300 mOsm). The extracellular solution was used as the wash, reference and compound delivery solution. The internal solution contained the following (in mM): NaCl 70, KF 70, KCl 10, EGTA 5, HEPES 5 and Escin 0.01 (pH=7.2, Osmolarity ~295 mOsm). Escin is made at a 5 mM stock in water, aliquoted, and stored at −20° C. The compound plate was created at 2× concentrated in the extracellular solution. The compound was diluted to 1:2 when added to the recording well. The amount of DMSO in the extracellular solution was held constant at the level used for the highest tested concentration. A holding potential of −80 mV with a 100 ms step to 0 mV was used. Mean current was measured during the step to 0 mV. 100 μM Bepridil was used to completely inhibit KCNT1 current to allow for offline subtraction of non-KCNT1 current. The average mean current from 3 sweeps was calculated and the % inhibition of each compound was calculated. The % Inhibition as a function of the compound concentration was fit with a Hill equation to derive $IC_{50}$, slope, min and max parameters. If KCNT1 inhibition was less than 50% at the highest tested concentration or if an $IC_{50}$ could not be calculated, then a percent inhibition was reported in place of the $IC_{50}$.

Results from this assay are summarized in Table 1 below. In this table, "A" indicates $IC_{50}$ of less than or equal to 1 μM.

TABLE 1

| Patent Compound No. | KCNT1-WT $IC_{50}$ (μM) |
|---|---|
| 1 | A |
| 2a | A |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A pharmaceutical composition comprising a compound of Formula I:

(I)

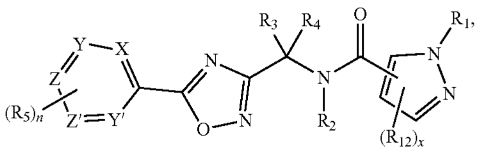

or a pharmaceutically acceptable salt thereof, wherein:

one of X, Y, Z, Y' and Z' is N and the other four are CH, wherein the hydrogen of CH may be substituted with $R_5$;

$R_1$ is selected from the group consisting of $C_{1-6}$alkyl, $C_{3-10}$cycloalkyl, 3-10 membered heterocyclyl, 3-10 membered heteroaryl, and phenyl, wherein $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, $C(O)N(R_9)_2$, $N(R_9)_2$, $C_{3-7}$cycloalkyl, phenyl, 3-10 membered heteroaryl, and $C_{1-6}$alkoxy;

$R_{12}$ is selected from the group consisting of $C_{1-6}$alkyl, $C_{3-10}$cycloalkyl, 3-10 membered heterocyclyl, 3-10 membered heteroaryl, and phenyl, wherein the $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, —OH, —CN, $C_{1-6}$alkyl, $C_{1-6}$haloalkyl, and $C_{1-6}$alkoxy; or two $R_{12}$ on adjacent carbons can be taken together with the two carbons where $R_{12}$ are attached to form a carbocyclic ring;

x is 0, 1 or 2;

$R_2$ is hydrogen or $C_{1-4}$alkyl;

$R_3$ is selected from the group consisting of hydrogen, $C_{1-6}$alkyl, $C_{3-10}$ cycloalkyl, 3-10 membered heterocyclyl, 3-10 membered heteroaryl, and phenyl; and $R_4$ is selected from $C_{1-6}$alkyl and hydrogen; or $R_5$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$ cycloalkyl, 3-10 membered heterocyclyl, 3-10 membered heteroaryl, phenyl, $C_{3-7}$cycloalkylene, or 3-7 membered heterocyclene may be optionally substituted with one or more $R_7$;

each $R_5$ is independently selected from the group consisting of $C_{1-6}$alkyl, $C_{1-6}$haloalkyl, $C_{1-6}$alkylene-$N(R_9)_2$, $C_{1-6}$alkylene-O—$C_{3-10}$cycloalkyl, $C_{1-6}$alkoxy, $C_{1-6}$alkoxy substituted with $C_{3-10}$cycloalkyl optionally substituted with one or more halogens, $C_{1-6}$haloalkoxy, 3-10 membered heterocyclyl optionally substituted with one or more halogens or $C_{1-6}$alkoxy, 3-10 membered heteroaryl, $C_{1-6}$alkylene-OH, $C_{1-6}$alkylene-$C_{1-}$ 6alkoxy, OH, $N(R_9)_2$, —$C(O)OR_8$, $C(O)N(R_9)_2$, $C_{1-6}$alkylene-CN, —CN, —$S(O)_2$—$C_{1-6}$alkyl, $C_{1-6}$alkylene-$S(O)_2$—$C_{1-6}$alkyl, —$S(O)_2$—$N(R_9)_2$, —OC(O)$C_{1-6}$alkyl, —O—$C_{3-10}$cycloalkyl optionally substituted with one or more halogen or $C_{1-6}$alkyl, and $C_{3-10}$cycloalkyl optionally substituted with one or more substituents selected from halogen, $C_{1-6}$alkyl, and $C_{1-6}$alkoxy;

n is selected from the group consisting of 0, 1, 2, and 3;

$R_7$ is each independently selected from the group consisting of phenyl, $C_{1-6}$alkoxy, —OH, —$N(R_9)_2$, —$NR_9$—$SO_2$—$C_{1-6}$alkyl, —O—($C_{1-6}$alkylene)-phenyl, $C_{3-10}$cycloalkyl, —$C(O)OR_8$, —$C(O)N(R_9)_2$, —$NR_{10}C(O)$—$R_{11}$, —CN, —$S(O)_2$—$C_{1-6}$alkyl, —$S(O)_2$—$N(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —$N(R_9)_2$;

$R_8$ is hydrogen or $C_{1-6}$alkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents each independently selected from halogen and —OH;

each $R_{10}$ is independently hydrogen or $C_{1-6}$alkyl; and $R_{11}$ is selected from the group consisting of $C_{1-6}$alkyl, $C_{1-6}$alkoxy, and —O—($C_{1-6}$alkylene)-phenyl;

and a pharmaceutically acceptable excipient.

2. The pharmaceutical composition of claim 1, wherein the compound is a compound of Formula I-a:

(I-a)

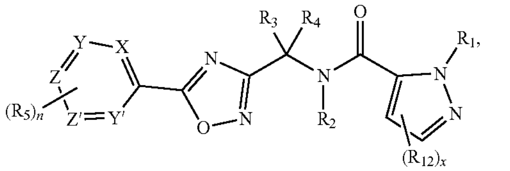

or a pharmaceutically acceptable salt thereof.

3. A compound of Formula III:

(III)

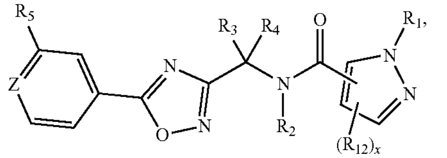

or a pharmaceutically acceptable salt thereof, wherein:

Z is CH or N;

$R_1$ is $C_{1-6}$alkyl;

$R_2$ is hydrogen or $C_{1-4}$alkyl;

$R_{12}$ is $C_{1-6}$haloalkyl;

x is 0, 1 or 2;

$R_3$ is $C_{1-6}$alkyl;

$R_4$ is $C_{1-6}$alkyl or H; and $R_5$ is $C_{1-6}$alkyl or $C_{3-6}$ cycloalkyl.

4. The compound of claim 3, wherein the compound is a compound of Formula III-a:

(III-a)

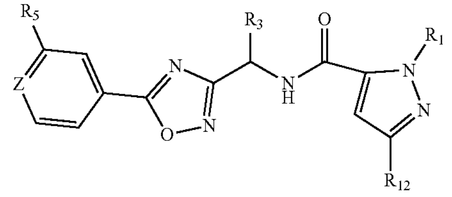

or a pharmaceutically acceptable salt thereof.

5. The compound of claim 4, selected from the group consisting of:

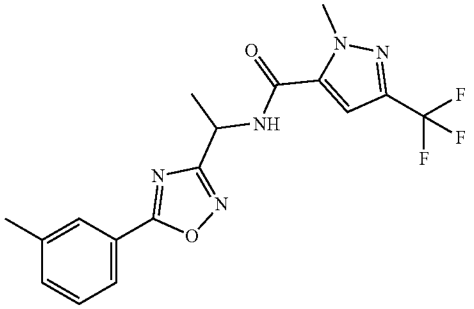

and

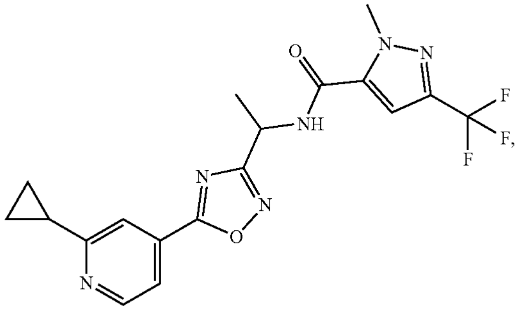

or a pharmaceutically acceptable salt thereof.

6. A pharmaceutical composition, comprising: a compound of claim 3, or a pharmaceutically acceptable salt thereof; and a pharmaceutically acceptable excipient.

* * * * *